(12) United States Patent
Stromblad et al.

(10) Patent No.: US 8,192,744 B2
(45) Date of Patent: Jun. 5, 2012

(54) DRUG FOR TREATING STATES RELATED TO THE INHIBITION OF ANGIOGENESIS AND/OR ENDOTHELIAL CELL PROLIFERATION

(75) Inventors: Staffan Stromblad, Huddinge (SE); Taavi Pall, Tabasalu (EE); Priit Kogerman, Tabasalu (EE)

(73) Assignee: IBCC Holding AS, Tallinn (EE)

( * ) Notice: Subject to any disclaimer, the term of this patent is extended or adjusted under 35 U.S.C. 154(b) by 0 days.

(21) Appl. No.: 12/660,886

(22) Filed: Mar. 5, 2010

(65) Prior Publication Data

US 2011/0009310 A1  Jan. 13, 2011

Related U.S. Application Data

(63) Continuation-in-part of application No. 10/487,620, filed as application No. PCT/SE02/15431 on Aug. 26, 2002, now abandoned.

(51) Int. Cl.
*A61K 38/16* (2006.01)
*A61K 39/00* (2006.01)

(52) U.S. Cl. .................. 424/184.1; 424/185.1; 514/21.2

(58) Field of Classification Search ........................ None
See application file for complete search history.

(56) References Cited

FOREIGN PATENT DOCUMENTS

WO   WO/2003/018044  *  6/2003

OTHER PUBLICATIONS

Pall et al. Recombinant CD44-HABD is a novel and potent direct angiogenesis inhibitor enforcing endothelial cell-specific growth inhibition independently of hyaluronic acid binding. Oncogene (2004) 23, 7874-7881.*

Bajorath, J. et al. 1998. Identification of CD44 Residues Important to Hyaluronan Binding and Delineation . . . J. Biol. Chem. 273(1) 338-343.

Bartolazzi, A. et al. 1994. Interaction between CD44 and Hyaluronate is directly implicated in the regulation.. J. Exp. Med. 180:53-66.

Gao, C.A.,et al. 1981. Metastasis suppression by the standard CD44 isoform does not require the binding . . . Cancer Rws. 58:2350-2352.

Brown, T. et al. 1991. Human Keratinosytes express a New CD44 Core protein (CD44E) as . . . The J. of Cell Biol. 113(1):207-221.

Auerbach , R. et al. 2003 Angiogenesis Assays: A critical overview. Clinical Chemistry 49(1): 32-40.

Yu, G and Stamenkovic, I. 1999. Localization of matrix metalloproteinase 9 to the cell surface . . . Genes & Development 13:35-48.

* cited by examiner

*Primary Examiner* — Maher Haddad

(74) *Attorney, Agent, or Firm* — Gearhart Law, LLC

(57) ABSTRACT

Soluble recombinant CD44 hyaluronic acid binding domain (CD44HABD) inhibits angiogenesis in vivo in chick and mouse and thereby inhibits human tumor growth of various origins. The anti-angiogenic effect of CD44-HABD is independent of hyaluronic acid (HA) binding, since non-HA-binding mutants of CD44HABD still maintain anti-angiogenic properties. The invention discloses soluble non glycosylated CD44 recombinant proteins as a novel class of angiogenesis inhibitors based on targeting of vascular cell surface receptor. A method of block of angiogenesis and treatment of human tumors using recombinant CD44 proteins as well as their analogues is disclosed. As a further embodiment of the invention, methods for screening for new drug targets using CD44 recombinant proteins and their analogues are presented.

14 Claims, 17 Drawing Sheets

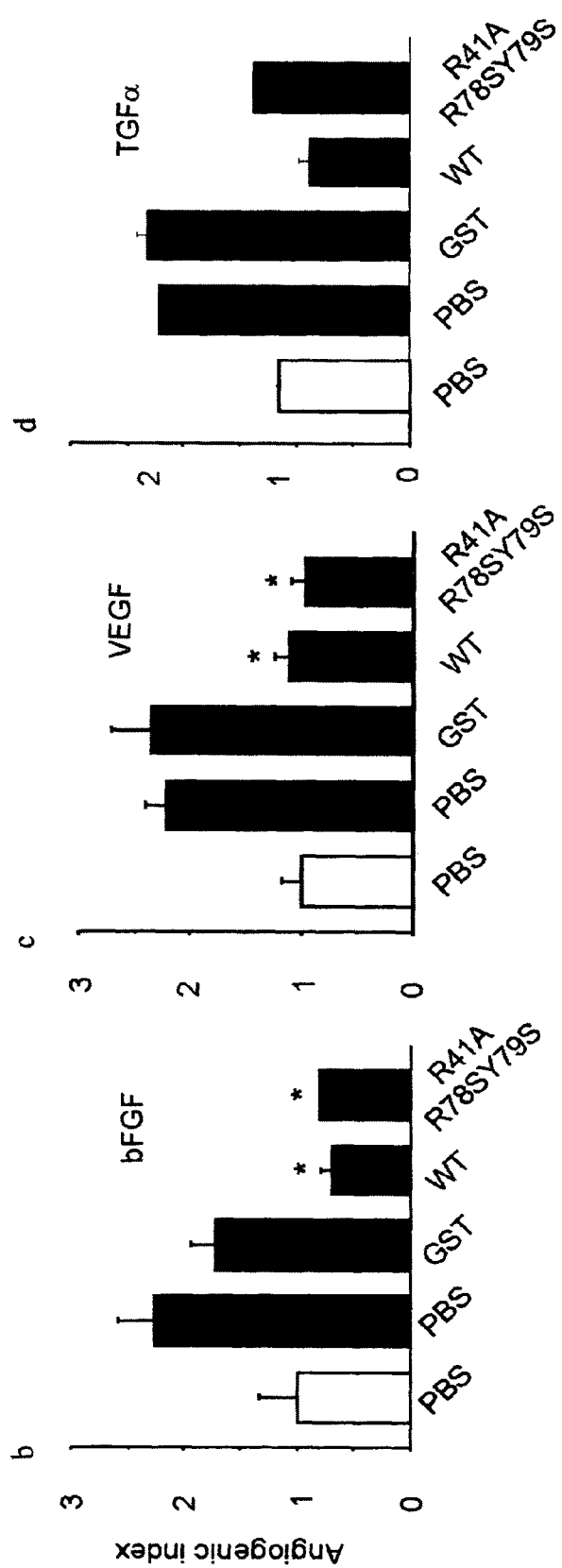
FIG. 3 B-D

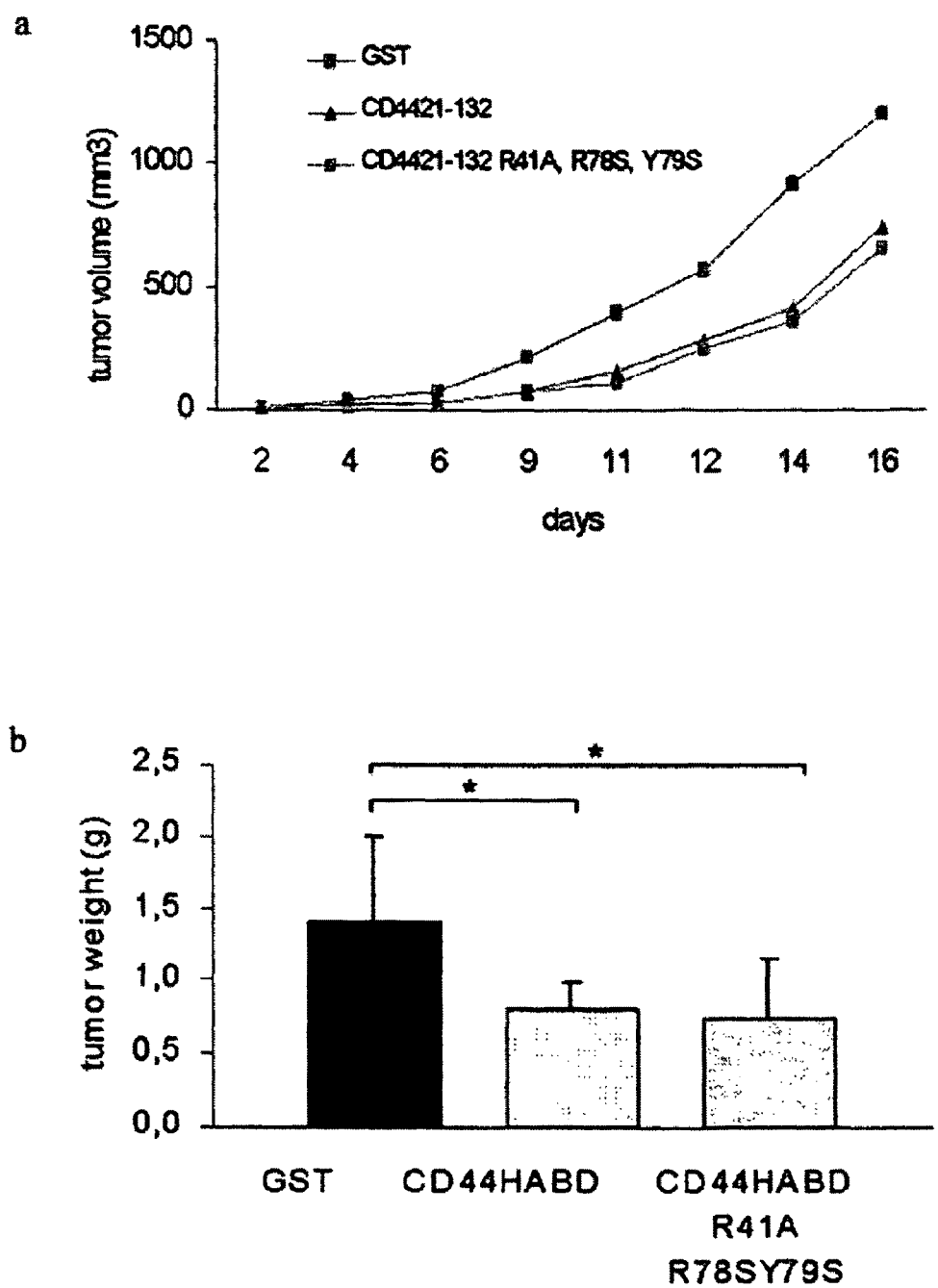
FIG. 5 A-B

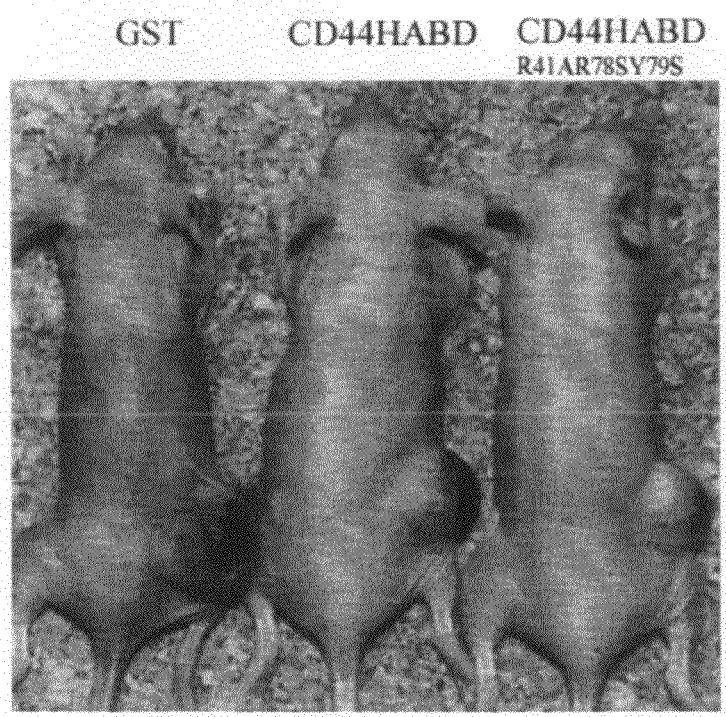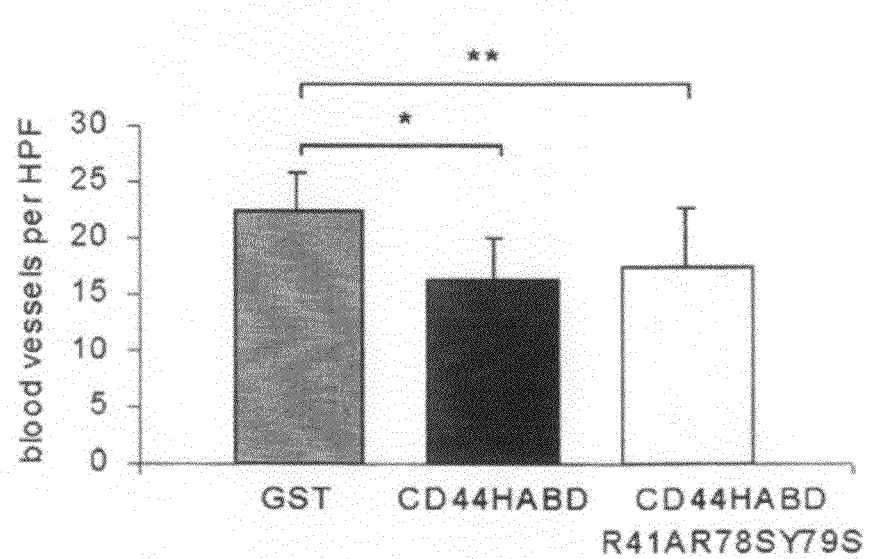
FIG. 5 C-D

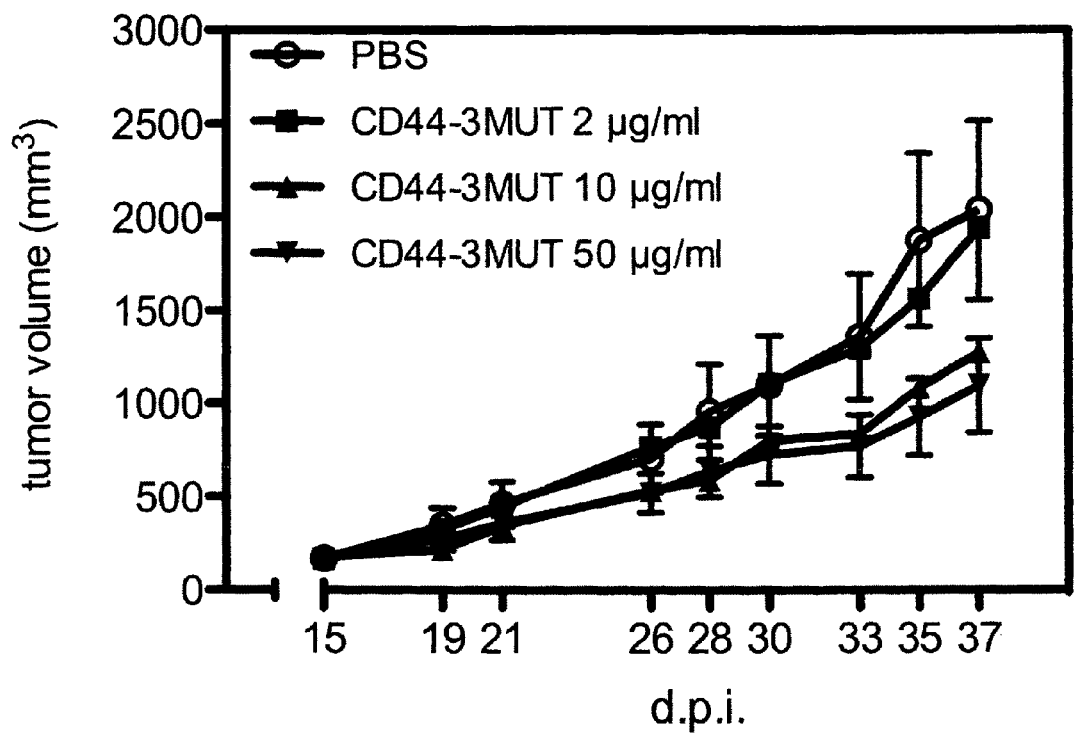
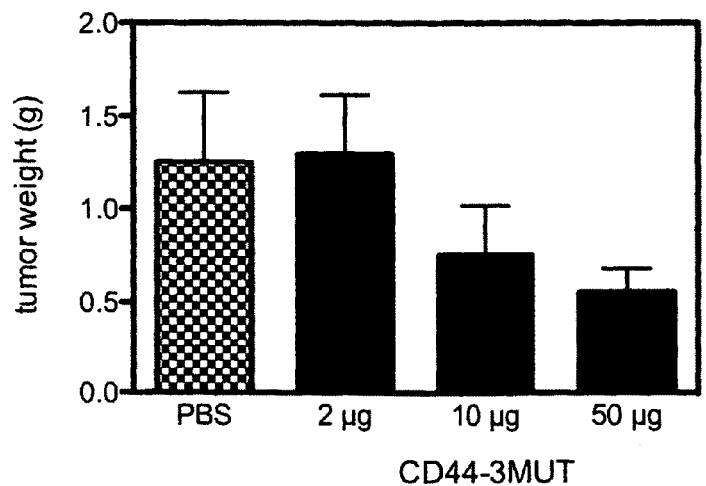
FIG. 8

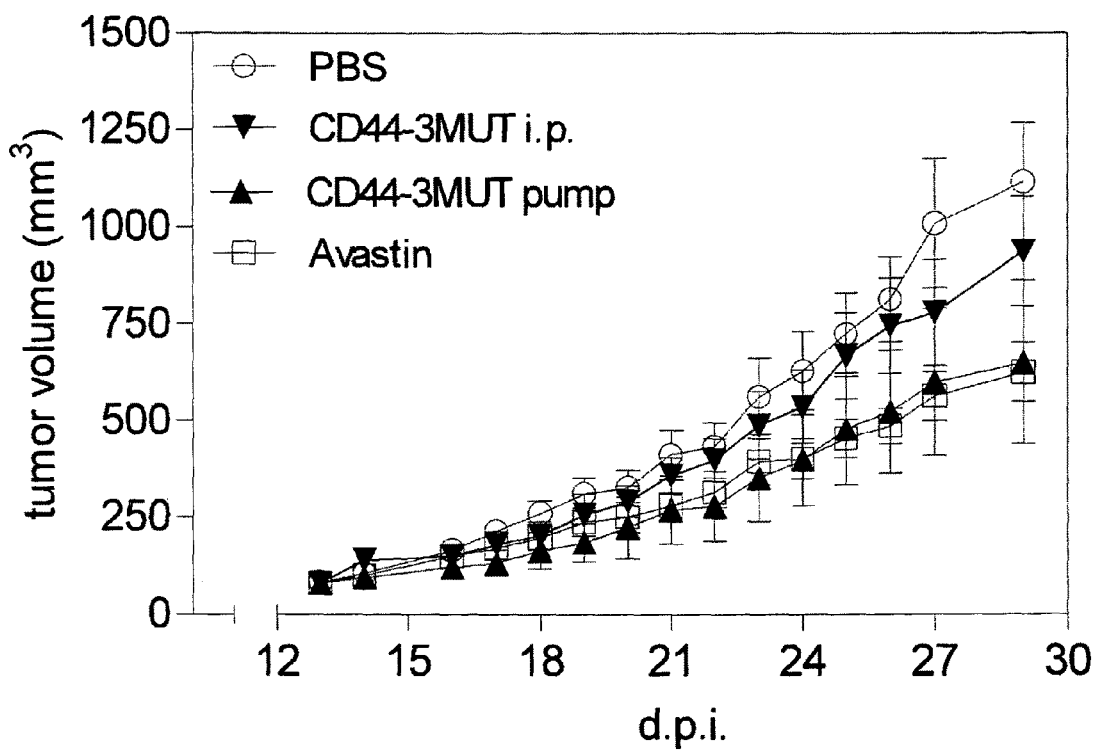
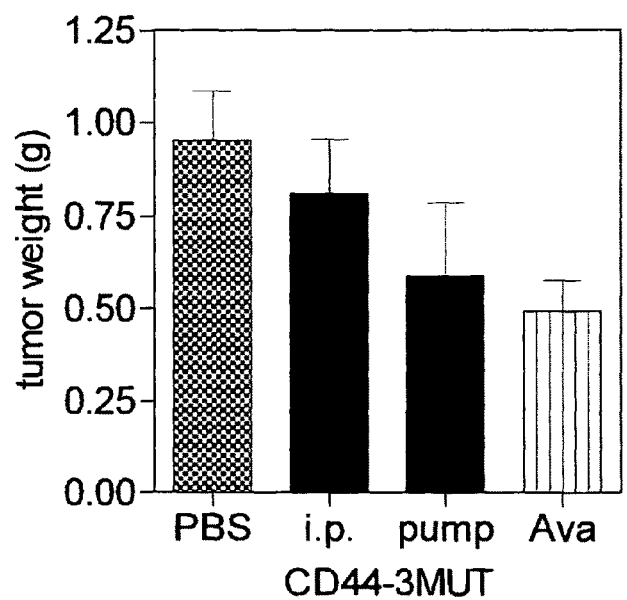
FIG. 9

DRUG FOR TREATING STATES RELATED TO THE INHIBITION OF ANGIOGENESIS AND/OR ENDOTHELIAL CELL PROLIFERATION

PRIORITY

This application is a continuation-in-part of the U.S. patent application Ser. No. 10/487,620 filed on May 24, 2004, now abandoned the priority of which is claimed, and which is a national application of PCT/SE02/015431, filed on Aug. 26, 2002 and published as WO2003/018044 on Mar. 6, 2003, the priority of which is also claimed.

SEQUENCE LISTING

This application contains sequence data provided on a computer readable diskette and as a paper version. The paper version of the sequence data is identical to the data provided on the diskette.

TECHNICAL FIELD

The invention refers to the use of a molecule comprising the CD44-hyaluronic acid binding domain for a drug and manufacturing the drug. Furthermore, the invention relates to a method for screening for substances binding to the molecule comprising the CD44-hyaluronic acid binding domain.

TECHNICAL BACKGROUND

The formation of new blood vessels by angiogenesis is a central event in many different pathological states, including ocular diseases causing blindness, such as macular degeneration, diabetic retinopathy and states of retinal hypoxia, states of chronic inflammation, such as rheumatoid arthritis, in psoriasis, atherosclerosis, restenosis, as well as in cancer growth and metastasis. In addition, hemangioma is caused by uncontrolled proliferation of endothelial cells. Given that many of these diseases are of a chronic nature and presently lack satisfactory cure, search for treatments and drugs against these diseases is very important. According to current paradigm all solid tumors need to induce angiogenesis to cover their metabolic needs and grow over millimeter size. Therefore a possibility to inhibit tumor growth by reducing the neovascularization within tumor tissue would be most useful as adjuvant therapy for cancer cure. To this end, an agent blocking angiogenesis has the potential to constitute a medicament for all these common angiogenesis- (and/or endothelial cell-) dependent diseases.

One interesting target for drugs against diseases of this kind has been CD44 (Naot et al., Adv Cancer Res 1997; 71:241-319). CD44 is a cell surface receptor for the large glycosaminoglycan of the extracellular matrix hyaluronic acid (HA) (Aruffo et al., Cell 1990; 61:1303-13). CD44 plays a role in various cellular and physiological functions, including adhesion to and migration on HA, HA degradation and tumor metastasis. The CD44 receptor shows a complex pattern of alternative splicing in its variable region of the extracellular domain (Screaton et al., PNAS 1992; 89: 12160-4). CD44 is able to bind matrix metalloproteinase-9 (MMP-9) and can thereby localize MMP-9 to the cellular membrane, which may in part explain its activity in promoting tumor cell invasion and metastasis (Yu, 1999).

Among patent references disclosing CD44 and its connection to diseases described above may U.S. Pat. Nos. 6,025, 138, 5,902,795, 6,150,162, 6,001,356, 5,990,299 and U.S. Pat. No. 5,951,982 be mentioned.

WO94/09811 describes the use of CD44 in treating inflammation or detecting cancer metastasis of hematopoietic origin. Use of CD44 for inhibiting solid tumor growth or angiogenesis is not disclosed. WO 99/45942 discloses the use of HA-binding proteins and peptides including CD44 to inhibit cancer and angiogenesis-dependent diseases. CD44 is mentioned as one example of a long list of HA-binding proteins. In both publications the use of CD44 is limited to its ability to bind hyaluronic acid.

Ahrens et al. (Oncogene 2001; 20; 3399-3408) discloses that soluble CD44 inhibits melanoma tumor growth by blocking the binding of tumor cell surface CD44 to hyaluronic acid. Thus, this work teaches a hyaluronic acid binding dependent mechanism for the CD44 effect directly on melanoma tumor cell growth.

Alpaugh et al. (Exp. Cell Res. 261, 150-158 (2000)) discloses myoepithelial-specific CD44 and its antiangiogenic properties. This study deals with HA-binding properties of CD44.

Bajorath (PROTEINS: Structure, Function, and Genetics 39: 103-111 (2000)) discloses CD44 and its binding to HA, cell adhesion and CD44-signalling. Moreover, CD44 mutagenesis experiments are disclosed involving among others the well-established non-HA-binding mutations R41A and R78S, and their impact on CD44-binding to HA.

Bartolazzi et al. (1994) discloses an experiment where mammalian cell expressed CD44HRg-molecule inhibits tumor growth in nude mice. A mutant molecule CD44-R41A-Rg, not mediating cell attachment to hyaluronate, also expressed from mammalian cell did not have similar effect.

Thus, the prior art discloses the potential use of CD44 to specify that any effects are dependent on HA-CD44-interaction. Consequently, all utility ascribed this far to CD44-derived peptides is directly dependent on their ability to bind hyaluronic acid.

Given that hyaluronic acid is widely expressed in the body at high levels, a treatment based on inhibition of this extracellular component result in a high risk for unwanted side effects outside of the tumor. Furthermore, because of the high total amounts of HA in the body, such strategy will require high doses of HA-blocking recombinant proteins, thus even further increasing the risk for side effects.

Accordingly, a need exists for finding novel drugs for treating tumors, as well as novel pathways for the relation between CD44 and tumor growth, in order to provide new drug targets, which avoid the side effects described above.

There is also a clear need for a drug that could be administered in substantially smaller doses than substances having primary effect on CD44-HA binding function.

In addition, there is a need to develop novel inhibitors of angiogenesis, as these constitute potential medicaments not only for cancer, but also for an array of common diseases as disclosed above. To this end, it is important to elucidate the relation between CD44 and angiogenesis, in particular the potential direct effects of CD44 on the vasculature and on the various diseases that are dependent on new blood vessel formation.

SUMMARY OF THE INVENTION

Kogerman et al. (Oncogene 1997; 15: 1407-16) found that mouse fibrosarcoma cells stably expressing human CD44 standard isoform (hCD44s) had lost their hCD44s expression in large subcutaneous tumors. When hCD44s negative cells from these primary tumors were reintroduced subcutaneously into new mice for second round of tumor growth, then resulting tumors had significantly shorter latency times than hCD44s positive tumors.

The observed longer latency times for hCD44s expressing tumors lead the inventors to realize that the inhibitory effect of hCD44s over expression in subcutaneous tumor growth is connected to inhibition of tumor angiogenesis. Induction of angiogenesis is essential for growth and persistence of solid tumors and their metastases. In the absence of angiogenesis, tumors cannot grow beyond a minimal size and remain dormant in the form of micrometastases (Holmgren et al., Nat Med 1995; 1: 149-53). The inventors disclose here that recombinant soluble human CD44 hyaluronic acid binding (CD44HABD) domain inhibits angiogenesis in vivo in chick and endothelial cell proliferation in vitro, and thereby blocks human tumor growth in chick and mice. The inventors describe a novel type of angiogenesis inhibitor, as they found that recombinant cell surface receptor CD44 inhibits angiogenesis and tumor growth in vivo and endothelial cell proliferation in vitro. Furthermore, the inventors have created mutant forms of CD44 that are surprisingly also capable of inhibiting angiogenesis. The mutant forms were found to inhibit tumor growth in vivo and the effect is dose-dependent. The advantage with these mutants of CD44 is that they do not bind HA, demonstrating that the mechanism for inhibition of angiogenesis is unexpectedly independent of binding to HA. Importantly, use of mutant CD44 for systemic administration as a medicament will be more specific for angiogenesis, since it will not be bound up by HA in the body, and can therefore be used at lower doses and has less risk of causing unwanted side effects.

Accordingly, the invention relates to the use of a molecule comprising a non-HA-binding variant of the CD44-hyaluronic acid binding domain, as well as analogues and recombinant variants thereof, including the specified mutants, for treating states related to the inhibition of angiogenesis and manufacturing of a medicament for treating such states. Moreover, the invention relates to a method for screening for molecules binding to the CD44-hyaluronic acid-binding domain, thereby being potential targets for inhibiting angiogenesis and for cell proliferation. Further, the invention relates to a kit for carrying out the screening method, as well as the molecules found by the method. Also, the invention relates to a molecule comprising a non-HA-binding variant of the CD44-hyaluronic acid binding domain, as well as analogues, recombinant and mutated variants thereof for targeting of endothelial cells.

According to this disclosure, drugs for treating states related to angiogenesis, such as various cancerous states, can be easily provided, taking advantage of the novel mechanisms presented herein. Furthermore, through the method of screening, other molecules may be found, which affect cell proliferation and/or angiogenesis.

SHORT DESCRIPTION OF THE DRAWINGS

FIG. 1 shows a SDS PAGE of recombinant GST and GST-CD44 proteins. The gel was stained with Coomassie Brilliant Blue. Molecular weight markers are shown on the right.

FIG. 5 shows that recombinant CD44HABD inhibits CD44 negative melanoma growth. a, Growth curve of s.c. SMMU-1 tumors in nude mice treated with CD44HABD, CD44HABD$^{R41AR78SY79S}$ or GST as control, n=8 per group. b, Tumor weights at day 16, where the black line represents the median value. c, Representative photographs of mice at day 16, treated as indicated. d, Blood vessel density at tumor border per high power field (HPF). *($P<0.005$), **($0.05$) significant results.

Figure 6:
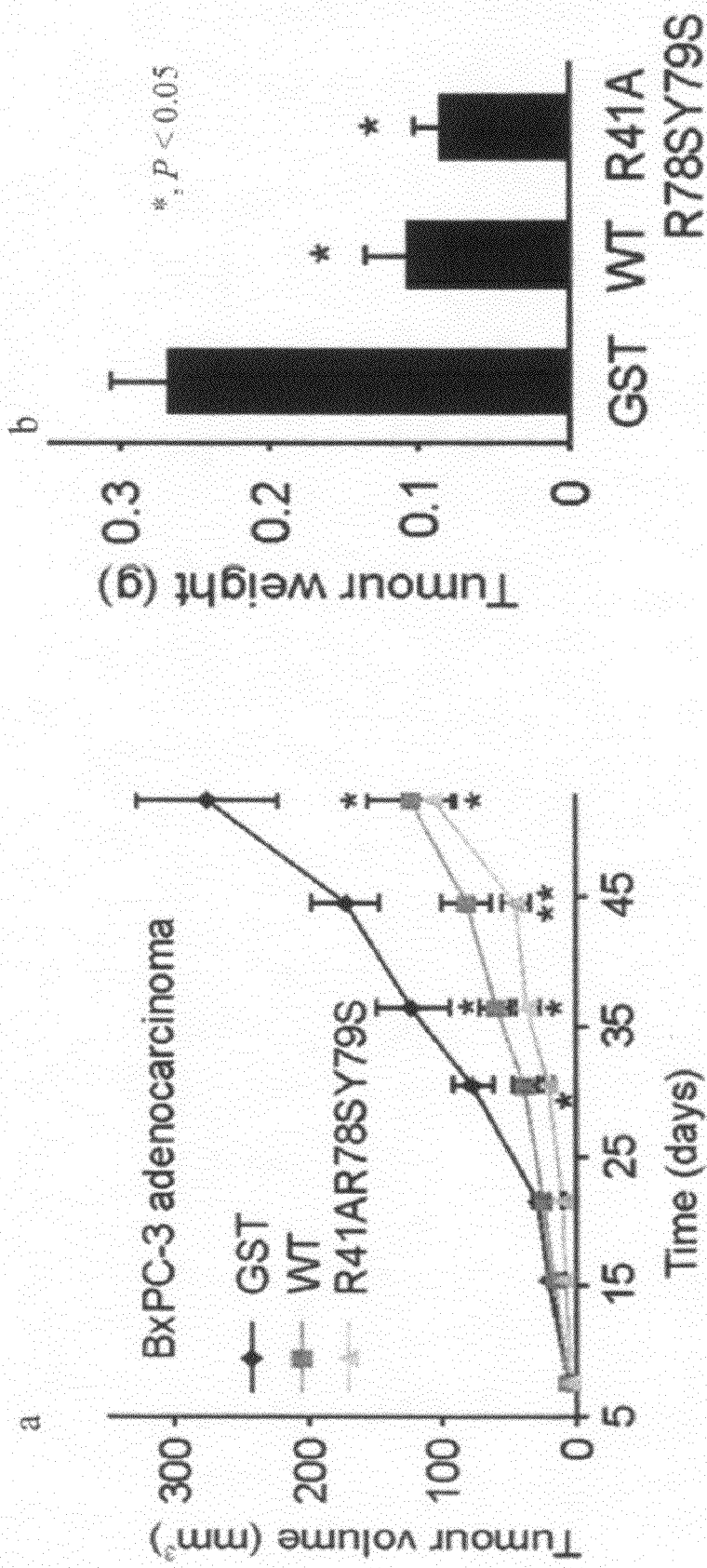

FIG. 6. CD44-HABD fusion proteins inhibit the growth of human pancreatic cancer cells in nude mice. BxPC-3 pancreatic adenocarcinoma (a) tumors in nude mice treated with GST-CD44HABD (solid rectangular), GST-CD44HABD$^{R41AR78SY79S}$ (solid triangle) or GST (diamond-solid) as control (n=6-7). b, average BxPC-3 tumor weights at the end of experiment. Values in graphs and bars represent mean+/−s.e.m. Asterisk indicates $P<0.05$.

Figure 7:
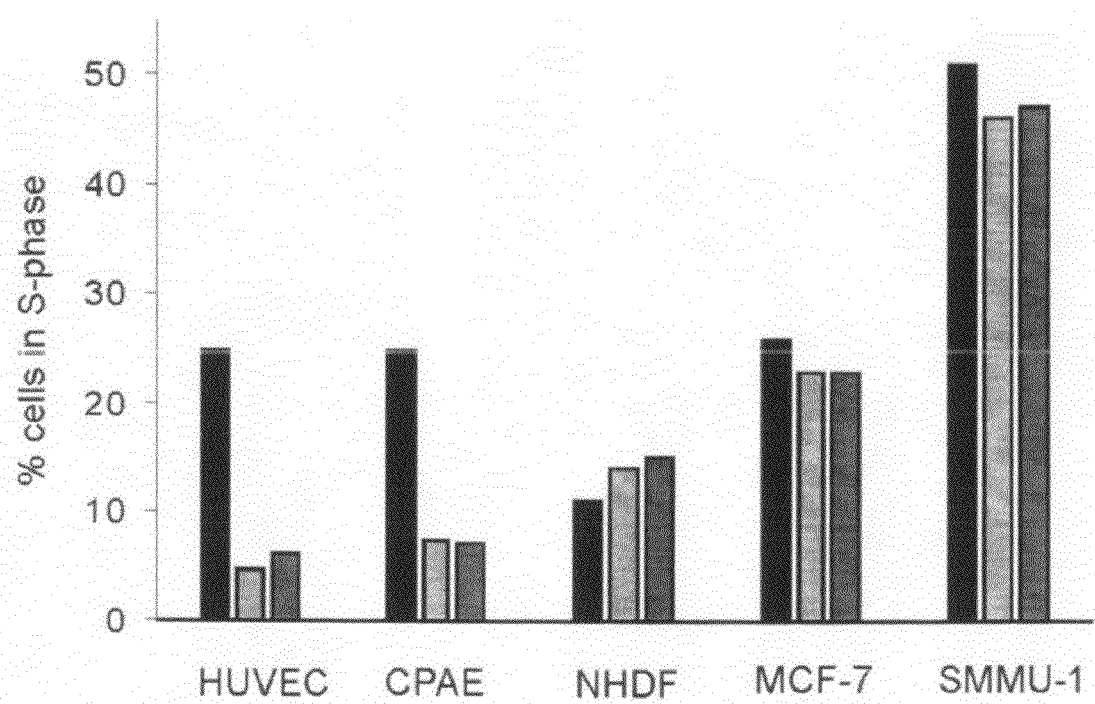

FIG. 7. Recombinant CD44HABD blocks specifically endothelial cell cycle. The proportion of cells in S-phase when treated with GST (black), GST-CD44HABD (pale gray) or GST-CD44HABD$^{R41AR78SY79S}$ (gray).) HUVEC, human vascular endothelial cells; CPAE, cow pulmonary arteria endothelial cells; NHDF, normal human dermal fibroblasts; MCF-7, human breast carcinoma cells.

FIG. 8. shows tumor growth assay with Hep3b human hepatoma cells in nude mice. Hep3b cells ($3.5 \times 10^6$) were injected subcutaneously into Foxn1 athymic nude mice. Intraperitoneal treatment with drugs started on day 14 post inoculation when the average tumor volume reached 150 mm$^3$. CD44-3MUT and PBS (phosphate buffered saline) were administered thrice a week. Tumor length (L) and width (W) were measured throughout the study. Tumor volumes were calculated using formula $V=L*W^2/2$. Final weight of dissected tumors was measured. Panel A, growth curves of tumors treated with different doses of CD44-3MUT. Panel B, average tumor weights at the end of experiment. Error bars indicate SEM.

FIG. 9 Tumor growth assay with Hep3b human hepatoma cells in nude mice. Hep3b cells ($5 \times 10^6$ cells) were injected subcutaneously into Foxn1 athymic nude mice. 14 days after inoculation, the average tumor volume reached 85 mm$^3$, mice were grouped into 4 groups. In one group CD44-3MUT was administrated 1 μg/mouse after every 12 hours by intraperitoneal injection. Another three groups of mice were anesthetized and 100 μl osmotic-pumps were implanted into intraperitoneal cavity through the midline abdominal incision. Before implantation pumps were filled with treatment solutions: PBS; Avastin (AVA) 400 μg/pump (approximate drug release from pump is 28.6 μg/day); CD44-3MUT 150 μg/pump (drug release 1.07 μg/day). Tumor length (L) and width (W) were measured throughout the study. Tumor volumes were calculated using formula $V=L*W^2/2$. Final weight of dissected tumors was measured. Panel A, growth curves of tumors treated with different administration methods of CD44-3MUT. Panel B, average tumor weights at the end of experiment. Error bars indicate SEM. Experiments have been performed by Celecure as blind experiments.

Figure 10:
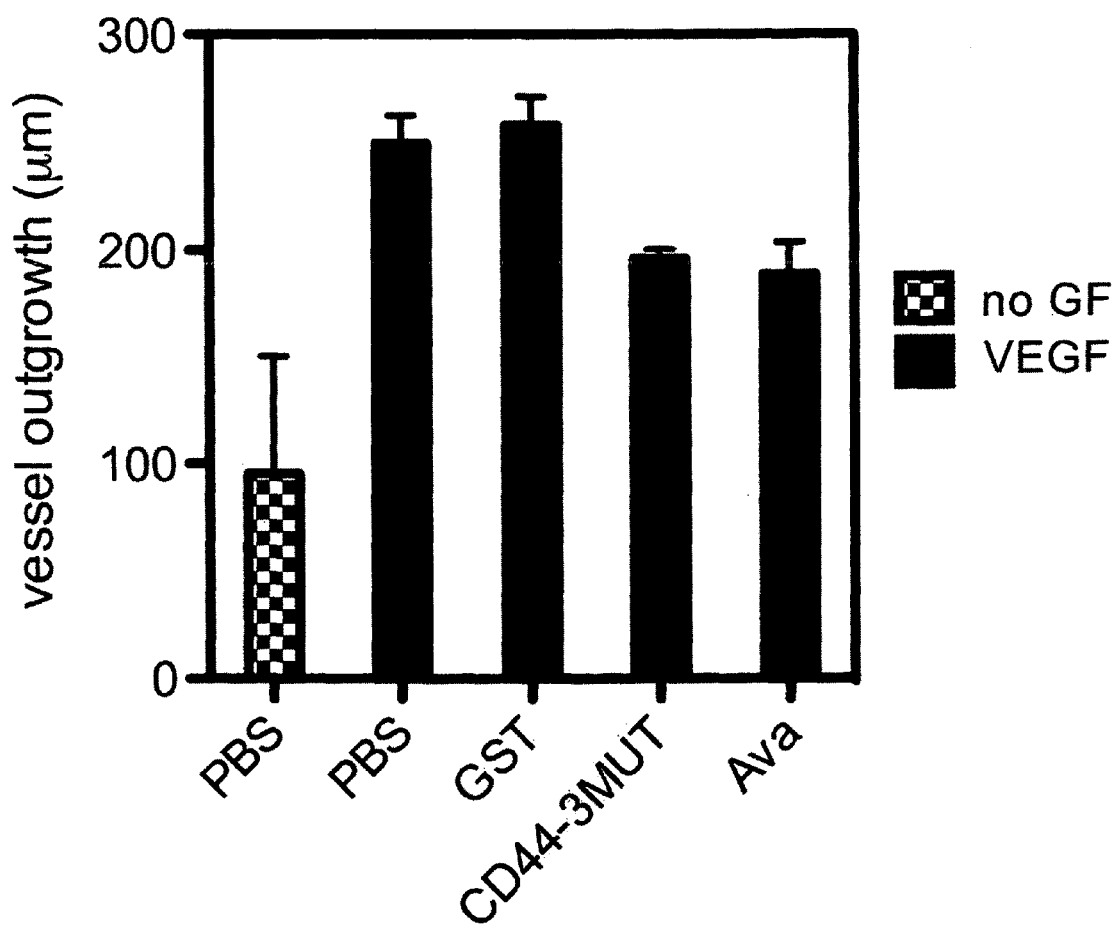

FIG. 10 Angiogenesis assay with chick aortic fragments. Aortic fragments were dissected from 14-day old chick embryo and embedded into collagen-I matrix containing VEGF and respective proteins. After 48 h of incubation photomicrographs were taken from aortic rings and blood vessel outgrowth was quantified on images by measuring vessel length from tip to aortic tissue. CD44-3MUT inhibits significantly VEGF-induced blood vessel growth (p=0.002, one-way ANOVA, n=4 independent experiments).

Figure 11:
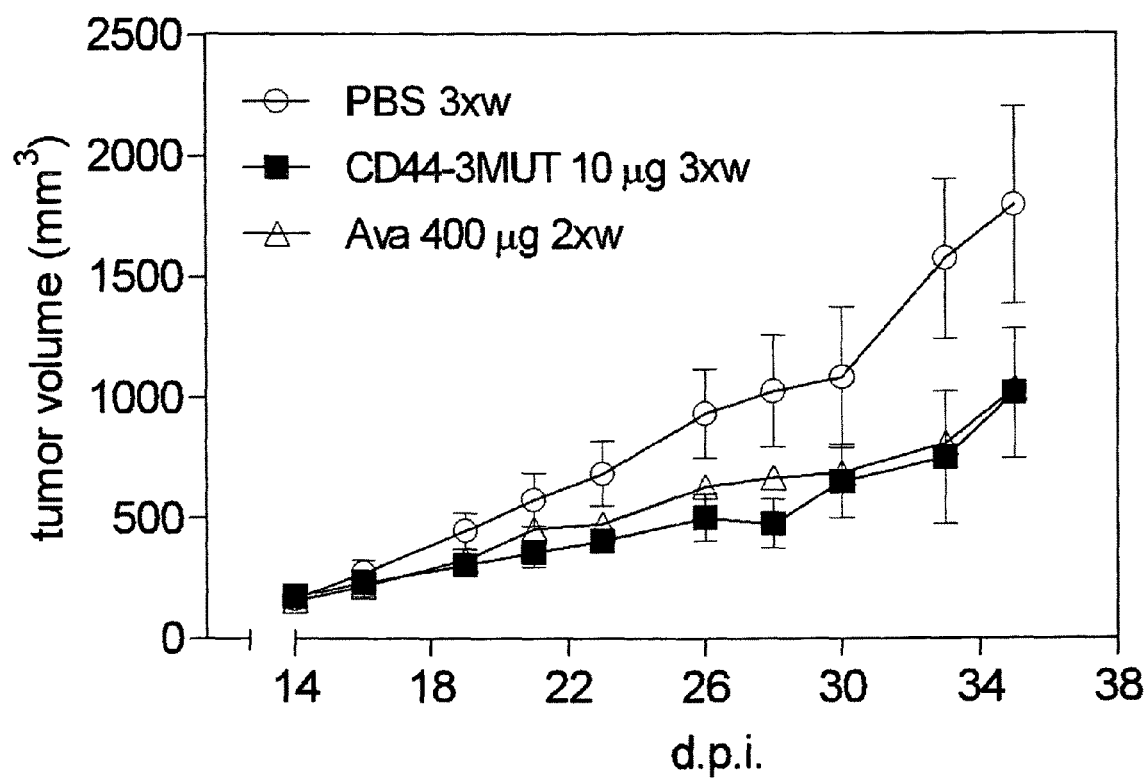

FIG. 11 Tumor growth assay with Hep3b human hepatoma cells in nude mice. Hep3b cells ($3.5 \times 10^6$) were injected subcutaneously into Foxn1 athymic nude mice. Intraperitoneal treatment with drugs started on day 14 post inoculation when average tumor volume reached 150 mm$^3$. CD44-3MUT was injected in the dose 10 μg per animal (0.4 mg/kg) thrice a week and Avastin dosing was used 400 μg per animal twice a week.

Figure 12:
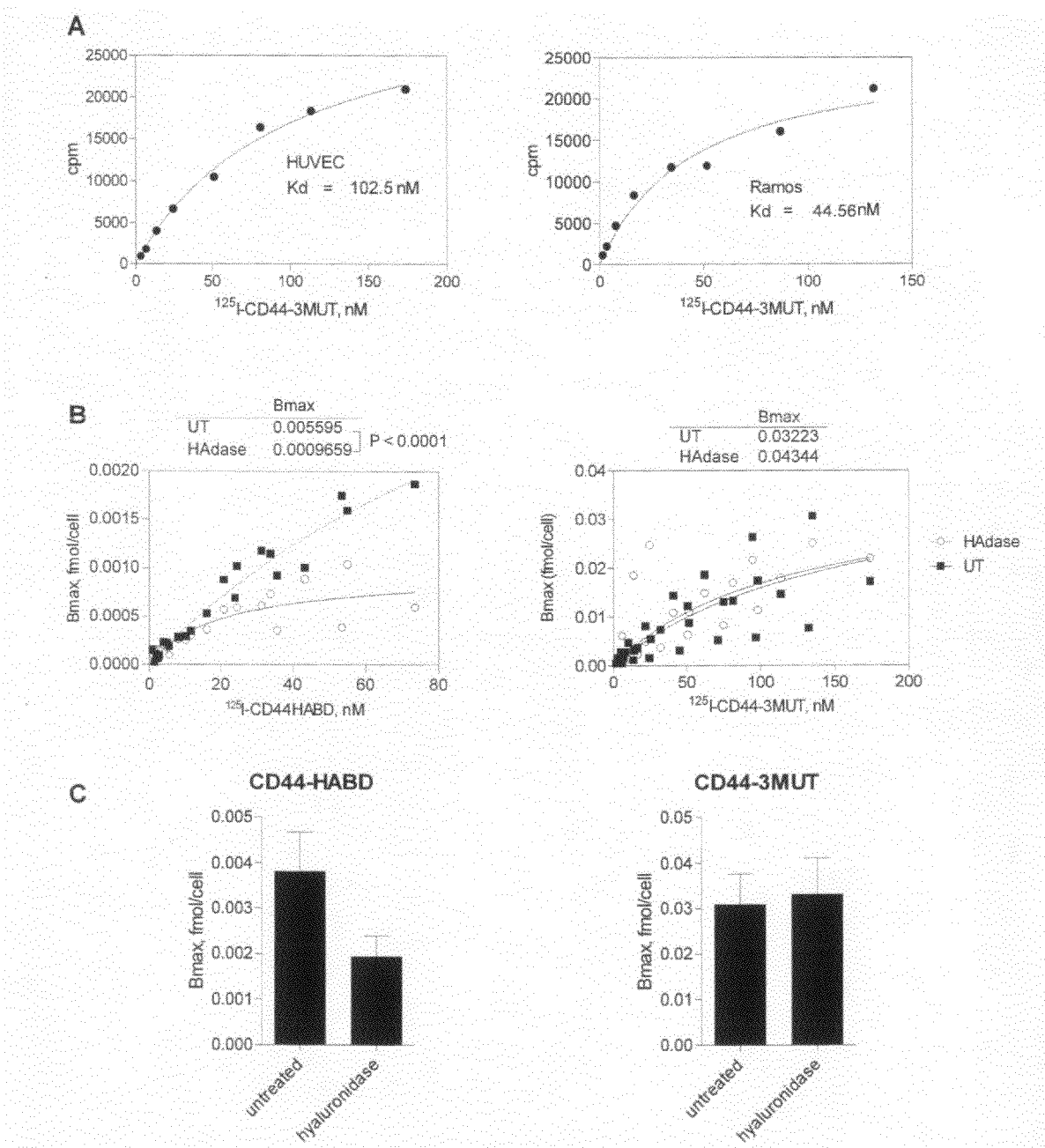

FIG. 12 Saturation binding of iodine-125 labeled CD44-3MUT. Cells were incubated 1 h with different concentrations of 125-I labeled CD44-3MUT. Bound radioactivity was quantified by a γ-counter. (A) Binding curves of representative experiment of HUVEC endothelial cells (left) and Ramos lymphoma cells (right). Kd-s were calculated using non-linear fit of specific binding. (B) Enzymatic degradation of hyaluronan reduces significantly CD44-HABD cellular binding (left panel), whereas CD44-3MUT binding remained unchanged. Curve was fitted to global specific binding data using non-lin fit. Statistical analysis was performed using extra sum of squares F-test. (C) Bmax of CD44-HABD and CD44-3MUT on HUVEC. Bars show mean±SE (n=3). Abbreviations: UT, untreated; Hadase, hyaluronidase; 3MUT, CD44-3MUT; HABD, CD44-HABD.

Figure 13:
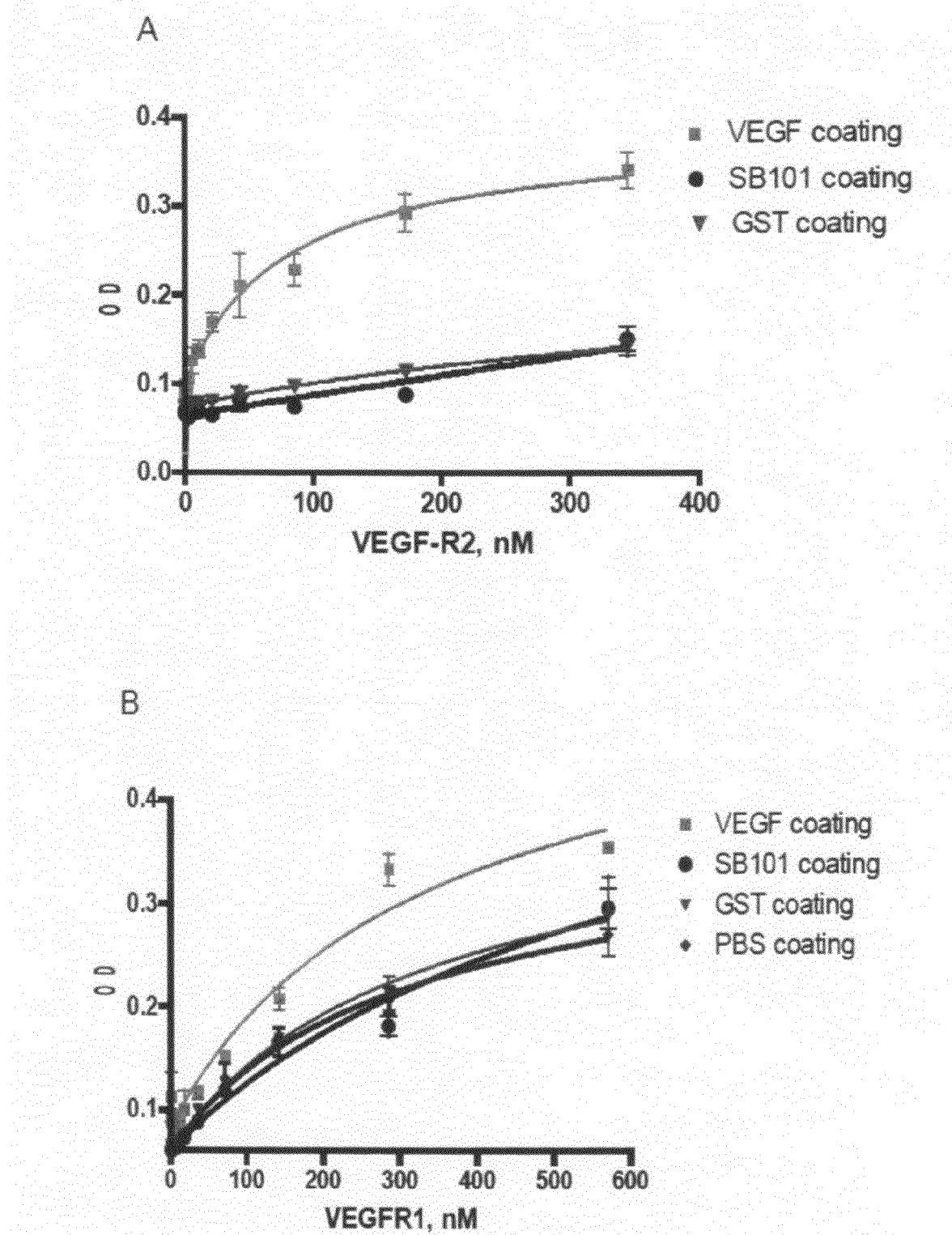
Figure 14:
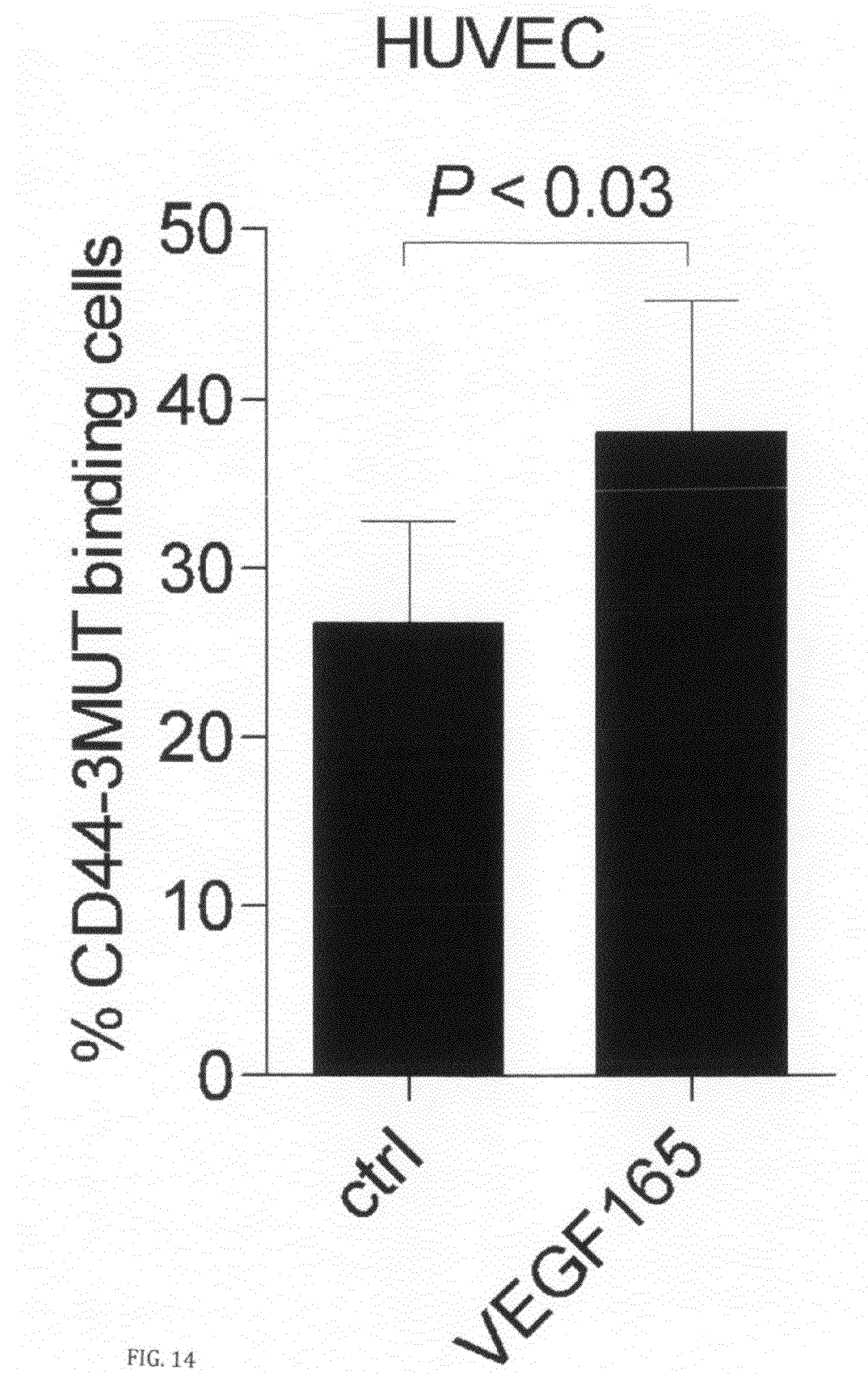

FIG. 13 Test of CD44-3MUT binding to VEGF receptors. Modified ELISA tests to evaluate the binding of VEGFR2 (panel A) and VEGFR1 (panel B) to immobilized CD44-3MUT. ELISA plate wells were coated with VEGF, as positive control and GST (Glutathione-S-transferase), PBS or CD44-3MUT. Nonspecific binding was blocked with 2.5% non-fat dry milk solution. VEGFR1 and VEGFR2 were added into the coated wells and incubated for 1 h at RT. VEGFR binding was detected with anti-VEGFR antibodies FIG. 14 CD44-3MUT binding to growth factor treated endothelial cells. Serum starved HUVEC were induced 30 min with VEGF165, followed by incubation with directly fluorescence-labeled CD44-3MUT at 4° C. CD44-3MUT binding by HUVEC was analyzed by FACS. Bars represent percentage of cells binding CD44-3MUT (mean±SE, n=5). Statistical analysis was done using two-tailed paired t-test.

Figure 15:
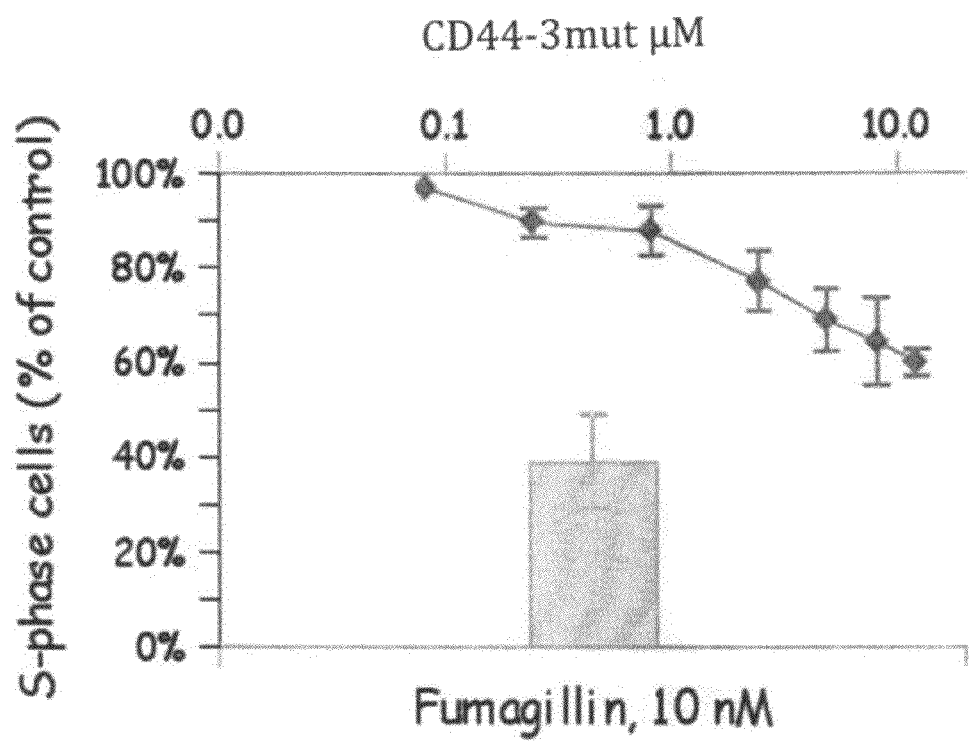

FIG. 15 Cell proliferation assay of HUVE cells. CD44-3MUT inhibits endothelial cell proliferation in dose-dependent fashion. Exponentially growing HUVE cell populations were treated with respective proteins for 24 h. Cells were double-stained with propidium iodide and BrdU and analyzed by FACS.

DEFINITIONS

The "hyaluronic acid binding domain" is hereafter referred to as HABD.

By a "non-HA-binding variant" of HABD is meant a variant that is modified by way of mutation or in any other way, so that it at least partly has lost its ability to bind to HA, but still has the capacity to inhibit angiogenesis and/or endothelial cell proliferation.

"Molecule" means here the smallest particle of a substance that retains the chemical and physical properties of the substance and is composed of two or more atoms; a group of like or different atoms held together by chemical forces.

Accordingly "Administering soluble human CD44HABD molecule" does not include injecting cells. The pharmaceutical composition could be adapted to oral or parenteral use, and could be administered to the patient as tablets, capsules, suppositories, solutions, suspensions or the like.

CD44HABD$^{R41A R78S Y79S}$ refers to a non HA binding triple mutant of the CD44HABD and is synonymous to CD44-3MUT. The molecule is according to SEQ ID NO:12.

By "analogues and recombinant variants" of a molecule comprising the CD44HABD, are meant molecules, such as fusion proteins, comprising the CD44HABD, thereby at least partly exerting essentially the properties of the CD44HABD.

By "states related to the inhibition of angiogenesis and/or endothelial cell proliferation" are meant such states and diseases, which may be treated or affected by an inhibition of the angiogenesis and/or endothelial cell proliferation.

By "a binding partner" for a molecule comprising the CD44HABD is meant a molecule having affinity for CD44HABD or mutants thereof.

By "a receptor molecule, or a part of a receptor molecule" is meant a molecule acting as a receptor, or being part of a receptor.

By "a modified variant" is in the context of the invention meant any modification to a normal wt-molecule, such as deletions, insertions, substitutions, analogs, fragments or recombinant variants thereof.

DETAILED DESCRIPTION OF THE INVENTION

WO94/09811 describes the use of CD44 in treating inflammation or detecting cancer metastasis. The authors show that CD44 is upregulated in inflammatory conditions and CD44 peptides are capable of inhibiting T-cell activation. No data or claims are presented on inhibition of metastasis by CD44 and no claims are made towards use of CD44 for inhibiting tumor growth or angiogenesis. WO 99/45942 discloses the use of HA-binding proteins and peptides including CD44 to inhibit cancer and angiogenesis-dependent diseases. This publication uses metastatin, a 38 kDa fragment of the cartilage link protein as well as a HA-binding peptide derived from this fragment to inhibit pulmonary metastasis of B 16 mouse melanoma and Lewis lung carcinoma. In the case of the HA-binding peptide, growth of B16 melanoma on chicken CAM and endothelial cell migration on HA have been inhibited. In both publications the use of HA-binding peptides is directly related to their ability to bind hyaluronic acid.

CD44 was previously implicated to promote angiogenesis by a mechanism dependent on its ability to bind matrix metalloproteinase-9 (MMP-9) (Yu and Stamenkovic, Genes Dev 1999; 13: 35-48; Yu and Stamenkovic, Genes Dev 2000; 14: 163-76). Over expression of soluble CD44 (sCD44v6-10) in murine TA3 mammary carcinoma cells inhibited the binding of MMP-9 to the tumor cell surface and thereby blocked tumor growth and vascularization (Yu and Stamenkovic 2000). MMP-9 was previously demonstrated to be involved in angiogenesis during development and in tumors (Vu et al., Cell 1998; 93: 411-22; Bergers et al., Nat Cell Biol 2000; 2: 737-44; Coussens et al., Cell 2000; 103: 481-90). CD44-MMP-9 complex is also implicated in activation of latent TGFβ since tubulogenesis in vitro was inhibited by block of TGFβ. (Yu and Stamenkovic, 2000).

The mutants of CD44-HABD used in this disclosure show very different affinities towards MMP-9 but independent of that, surprisingly they inhibit angiogenesis equally well. This makes it unlikely that MMP-9 binding is critical for the inhibition of angiogenesis as disclosed in the present invention. In addition, this disclosure describes a mechanism for CD44 that directly inhibits angiogenesis. Furthermore, the disclosure demonstrates a mechanism for CD44 that has a distinct target in normal endothelial cells, as compared to the previously proposed mechanism disrupting CD44-binding of MMP-9 at transformed tumor cell surfaces. Gao et al. (Cancer Res 1998; 58: 2350-2) show that metastatic ability, but not tumorigenicity of rat Dunning AT3.1 prostate cancer cells is independent of HA binding, as over expression of rat CD44 standard isoform and R44A non-HA-binding mutant both reduced dramatically formation of metastatic lung colonies but not local tumor growth. This suggests that other CD44 binding partners distinct from HA must be involved in metastasis. A number of CD44-binding proteins have been described including HGF, bFGF, fibronectin, osteopontin, selectin to name a few. However, the binding of several of these proteins is dependent on the post-translational modifications of CD44 and/or the inclusion of alternative exons in CD44 that are not present in our recombinant fusion proteins. Also, many of these CD44-binding proteins are present in large amount in the body, making CD44-derivatives binding to any of these less useful as a drug, because of a high risk of side effects. In addition, none of the previously described proteins are unique for targeting vascular cells, neither do they block a pathway required specifically for the growth of endothelial cells. Accordingly, the pathway we suggest in this disclosure has not been described before. This disclosure discloses a method for identifying the binding partner of CD44 and the pathway that is relevant for the inhibition of angiogenesis and endothelial cell growth.

In a first aspect the invention relates to the use of a molecule comprising a non-HA-binding variant of the CD44HABD, as well as analogues, recombinant and mutated variants thereof, for the manufacturing of a medicament for treating states related to the inhibition of angiogenesis and/or endothelial cell proliferation.

In one embodiment, the CD44-HABD comprises at least one mutation, thereby rendering it non-HA-binding.

In a preferred embodiment, the mutation(s) is (are) chosen from F34A, F34Y, K38R, K38S, R41A, Y42F, Y42S, R46S, E48S, K54S, Q65S, K68S, R78K, R78S, Y79F, Y79S, N100A, N100R, N101S, Y105F, Y105S, S112R, Y114F, F119A, F119Y. Preferably, the mutations are chosen from one or more of R41A, R78S, Y79S. Also, deletion mutations resulting in any fragment of CD44 from 3 to 110 amino acids in length are potentially useful for the purposes of the invention. However, the skilled person easily realizes that any mutation to wild-type HA-binding CD44, which makes the CD44-HABD, or fragments thereof, at least partly non-HA-binding, such as one or more deletions, substitutions or additions, may be introduced in the CD44-HABD part, as long as the desired properties are achieved.

The CD44-HABD is a protein covering amino acids 21-132 of intact human CD44 molecule, or has high degree of homology to this region of human CD44. The chicken CD44-HABD is the most dissimilar HABD that has been isolated by the inventors, having a sequence homology of 55% to human HABD at the amino acid level. Thus, a high degree of sequence homology means at least approximately 55% amino acid homology, desirably at least 65% homology, and most desirably at least 75% homology.

According to a preferred embodiment the C44-HABD protein and its non HA binding mutations are produced in bacterial cell culture and thereby the protein is non-glycosylated form.

Furthermore, the molecule according to the invention refers to a deleted or in any other way changed or mutated form of the CD44-HABD protein, whereby the changed form exhibits essentially the same properties as the original CD44-HABD-protein, or the herein specified CD44-HABD-mutants, as measured by any one of the methods described here.

In a preferred embodiment, the molecule comprising the non-HA-binding variant of the CD44HABD is chosen from the group comprising: human CD44HABD (SEQ ID NO: 2), dog CD44HABD (SEQ ID NO: 4), chick CD44HABD (SEQ ID NO: 6), human CD44HABD$^{R41A}$ (SEQ ID NO: 8), human CD44HABD$^{R78SY79S}$ (SEQ ID NO: 10), and CD44HABD$^{R41AR78SY79S}$ (SEQ ID NO: 12), the sequences above further comprising at least one modification thereby making them non-HA-binding. Other variants are also possible, such as CD44HABD$^{R78S}$, CD44HABD$^{Y79S}$, as well as GST-CD44HABD-fusion proteins having the R41A, R78S or the.Y79S mutations.

CD44HABD$^{R41A}$, CD44HABD$^{R78SY79S}$ and CD44HABD$^{R41AR78SY79S}$ are preferred examples of mutated variants of CD44-HABD, wherein the letters/figures in superscript indicates the position and type of mutation.

GST-CD44HABD is a fusion protein of a GST-part and CD44HABD. Other possible fusion proteins may be chosen from the group comprising IgG, IgM, IgA, His, HA, FLAG, c-myc, EGFP. GST is a short for glutathione-S-transferase, being used as a tag for the purpose of being able to purify the fusion protein on a GST-binding column, as well as for the purpose of detection. GST occurs naturally as a 26 kDa protein (Parker, M. W. et al., J. Mol. Biol. 213, 221 (1990); Ji, X. et al., Biochemistry, 31, 10169 (1992); Maru, Y. et al., J. Biol. Chem. 271, 15353 (1996).).

Accordingly, in another embodiment, the recombinant variant is a fusion protein having a GST part and a CD44-HABD part, wherein the CD44-HABD-part is in a wild-type form or in a mutated form. Other tags than GST are also fully possible.

Preferably, the CD44-HABD has a homology to the sequence SEQ ID NO: 2 of at least 55%, more preferably at least 65%, even more preferably at least 75%. Most preferably, the CD44-HABD is a modified variant (non-HA-binding gene product) of the sequence SEQ ID NO: 1.

The invention may be used for all states related to the inhibition of angiogenesis and/or endothelial cell proliferation. States and diseases to be treated may be chosen from the following non limiting group: ocular diseases causing blindness, or impaired vision, such as macular degeneration, diabetic retinopathy and states of retinal hypoxia, states of chronic inflammation, such as rheumatoid arthritis, in psoriasis, atherosclerosis, restenosis, as well as in cancer growth and metastasis, as well as all forms of cancer diseases and tumors, such as a cancer of breast, prostate, colon, lung, skin, liver, brain, ovary, testis, skeleton, epithelium, endothelium, pancreas, kidney, muscle, adrenal gland, intestines, endocrine glands, oral cavities, head and neck, or other solid tissue origin, or being any form of leukemia, as well as in hemangioma. For instance, the invention may be used for mouse, rat, chick, dog, horse, cat, bovine animals and for all long-lived species in a normal zoo. Preferably, the invention is used for humans.

In still another aspect, the invention refers to a recombinant molecule comprising a GST-part and a CD44HABD part. The CD44HABD part may for example be mutated with one or more of the following mutations: F34A, F34Y, K38R, K38S, R41A, Y42F, Y42S, R46S, E48S, K54S, Q65S, K68S, R78K, R78S, Y79F, Y79S, N100A, N100R, N101S, Y105F, Y105S, S112R, Y114F, F119A, F119Y. Preferably, the mutations are chosen from one or more of R41A, R78S, Y79S. However, the skilled person easily realizes that any mutation to wild-type HA-binding CD44, which makes the CD44-HABD, or fragment thereof, at least partly non-HA-binding, such as one or more deletions, substitutions or additions, may be introduced in the CD44-HABD part, as long as the desired properties are achieved.

In a preferred embodiment, the CD44-HABD-part comprises a non-HA-binding variant of the CD44-HABD of any one of the amino acid sequences SEQ ID NO: 2, SEQ ID NO:4, SEQ ID NO:6, SEQ ID NO:8, SEQ ID NO:10, SEQ ID NO:12, the sequences above further comprising at least one modification thereby making them non-HA-binding.

In the most preferred embodiment, CD44HABD comprises at least three consecutive amino acids of the amino acids 23-132 of CD44. Basically, all fragments from 3-110 amino acids in size are potentially efficient, for example amino acids 23-25, 24-26, 25-27, etc., amino acids 23-26, 24-27, etc., 23-27, etc., 23-28, etc. Thus, all combinations of consecutive amino acids up to 110 amino acids of the original molecule are possible for the purposes of the invention, as the skilled man easily realizes, as long as they show the desired properties, as tested by the methods illustrated in the example section of this application In another embodiment, the CD44HABD part is encoded by a sequence having at least 55% homology, preferably 65% homology, more preferably 75% homology, most preferably being any one of the nucleotide sequences: SEQ ID NO:1, SEQ ID NO:3, SEQ ID NO:5, SEQ ID NO:7, SEQ ID NO:9, SEQ ID NO:11, whereby the nucleotide sequences are in a modified form (non-HA-binding gene product or peptide).

In another aspect, the invention refers to a pharmaceutical composition in order to inhibit angiogenesis and/or endothelial cell proliferation, characterized in that it comprises at least one molecule comprising the CD44HABD, as well as analogues, recombinant and mutated variants thereof, in mixture or otherwise together with at least one pharmaceutically acceptable carrier or excipient.

The pharmaceutical compositions are prepared in a manner known to a person skilled in the pharmaceutical art. The carrier or the excipient could be a solid, semi-solid or liquid material that could serve as a vehicle or medium for the active ingredient. Suitable carriers or excipients are known in the art. The pharmaceutical composition could be adapted to oral or parenteral use and could be administered to the patient as tablets, capsules, suppositories, solutions, suspensions or the like.

The pharmaceutical compositions could be administered orally, e.g. with an inert diluent or with an edible carrier. They could be enclosed in gelatin capsules or be compressed to tablets. For oral therapeutic administration the compounds according to the invention could be incorporated with excipients and used as tablets, lozenges, capsules, elixirs, suspensions, syrups, wafers, chewing gums and the like. These preparations should contain at least 4% by weight of the compounds according to the invention, the active ingredient, but could be varied according to the special form and could, suitably, be 4-70% by weight of the unit. The amount of the active ingredient that is contained in compositions is so high that a unit dosage form suitable for administration is obtained.

The tablets, pills, capsules, lozenges and the like could also contain at least one of the following adjuvants: binders such as microcrystalline cellulose, gum tragacanth or gelatin, excipients such as starch or lactose, disintegrating agents such as alginic acid, Primogel, corn starch, and the like, lubricants such as magnesium stearate or Sterotex, glidants such as colloidal silica dioxide, and sweetening agents such as saccharose or saccharin could be added or flavorings such as peppermint, methyl salicylate or orange flavoring. When the unit dosage form is a capsule it could contain in addition of the type above a liquid carrier such as polyethylene glycol or a fatty oil. Other unit dosage forms could contain other different materials that modify the physical form of the unit dosage form, e.g. as coatings. Accordingly, tablets or pills could be coated with sugar, shellac or other enteric coating agents. Syrup could in addition to the active ingredient contain saccharose as a sweetening agent and some preservatives, dyes and flavoring agents. Materials that are used for preparation of these different compositions should be pharmaceutically pure and non-toxic in the amounts used.

For parenteral administration the compounds according to the invention could be incorporated in a solution or suspension. Parenteral administration refers to the administration not through the alimentary canal but rather by injection through some other route, as subcutaneous, intramuscular, intraorbital, intracapsular, intraspinal, infrasternal, intravenous, intranasal, intrapulmonary, through the urinary tract, through the lactiferous tract in cattle, into an organ such as bone marrow, etc. Bone marrow may also be treated in vitro. These preparations could contain at least 0.1% by weight of an active compound according to the invention but could be varied to be approximately 0.1-50% thereof by weight. The amount of the active ingredient that is contained in such compositions is so high that a suitable dosage is obtained. The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetra-acetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic. For topical administration the compounds according to the invention could be incorporated in a solution, suspension, or ointment. These preparations could contain at least 0.1% by weight of an active compound according to the invention but could be varied to be approximately 0.1-50% thereof by weight. The amount of the active ingredient that is contained in such compositions is so high that a suitable dosage is obtained. The administration could be facilitated by applying touch, pressure, massage or heat, warms, or infrared light on the skin, which leads to enhanced skin permeability. Hirvonen et al., Nat Biotechnology 1996; 14: 1710-13 describes how to enhance the transport of a drug via the skin using the driving force of an applied electric field. Preferably, iontophoresis is affected at a slightly basic pH.

In yet another aspect, the invention relates to a method for the treatment of a cancerous tumor or any other disease related to angiogenesis and/or endothelial cell proliferation in a subject, comprising administrating a pharmaceutical dose of a molecule comprising the CD44HABD, as well as analogues, recombinant and mutated variants thereof.

By a subject is meant any mammal, including humans. A human subject is preferred.

In another embodiment, the invention may be used for treating other diseases and disorders characterized by excessive formation of blood vessels and/or uncontrolled endothelial cell proliferation. These include, but are not limited to, adult blindness, or impaired vision, caused by diabetic retinopathy or macular degeneration, psoriasis and various states of chronical inflammation and hemangioma.

CD44HABD or a fragment thereof can be obtained by any method of recombinant expression or chemical synthesis known in the art. According to most preferred embodiment it is expressed in bacterial cells as described in example 1. It can be cloned into baculovirus vectors and expressed in insect cells. Bacterially expressed proteins lack any posttranslational modifications and accordingly the putative N-linked glycosylation sites of CD44HABD are nonglycosylated in the recombinant protein. The proteins of this disclosure can however be also expressed in mammalian cells or in any other expression system, but in such case the recombinant protein would need to be modified to remove the glycosylation. The affinity tag can be added to the protein product and the protein can be purified using affinity chromatography with the selected tag. The affinity tags are well known in the art and include, but are not limited to, GST-tag, His-tag, S-tag, T7-tag, V5-tag, E2-tag, c-myc-tag, HA-tag, FLAG-tag. The protein may be expressed without any tag and be purified by immunoaffinity, ion exchange or gel filtration chromatography or a combination thereof. Furthermore, non-glycosylated CD44HABD, fragments thereof, or its analogues can be obtained by known methods of chemical synthesis including but not limited to solid-phase peptide synthesis. CD44HABD obtained by any of the described methods is included in the present invention.

In still another aspect, the invention relates to a method for screening for a binding partner for a molecule comprising the CD44HABD as well as analogues, mutants and recombinant variants thereof, comprising the steps of:

a) providing the molecule comprising the CD44HABD, or fragments thereof;

b) contacting a potential binding partner to said molecule; and c) determining the effect of said molecule on said potential binding partner.

Potential methods for screening comprise: (I) a) Incubation of CD44/HABD, CD44HABD analogues or mutants thereof with cells, cell lysates, cellular fractions, tissues, organisms, animals or parts of organisms or animals.

b) Purification and detection of CD44HABD binding partners (e.g. by affinity columns, gel electrophoreses, and any detection using antibodies or protein staining or isotopes or other means of detecting CD44HABD or tags connected to CD44HABD.

c) Identification of CD44HABD binding partners by localization in gel electrophoresis (e.g. 2D electrophoresis), use of mass spectroscopy, sequencing, antibodies or other means of identification.

d) Determining the effect of CD44HABD on identified binding partners or determining the effect of other interacting agents of said potential binding partner in vitro or in vivo.

e) Using an identified CD44HABD-binding partner to design novel inhibitors of cell proliferation and/or angiogenesis.

(II) a) Using CD44HABD as a bait for genetic screening of DNA, cDNA, phage, peptide, protein, cell or organism libraries or screening of synthetic peptide, protein, polysaccharide, lipid, heparan sulphate or proteoglycan libraries using CD44HABD, analogues or mutants thereof as a bait, b) Detection of CD44HABD binding partners by selection markers.

c) Identification of CD44HABD binding partners by sequencing, hybridization, restriction analysis, antibodies or by step-wise elimination within a library or by other means of identification.

d) Determining the effect of CD44HABD on identified binding partner or determining the effect of other interacting agents of said potential binding partner in vitro or in vivo.

e) Using an identified CD44HABD-binding partner to design novel inhibitors of cell proliferation and/or angiogenesis.

Moreover, the screening method of the invention may also be used for determining the effect of other activators or functional blocking agents of said potential binding partners.

Furthermore, a CD44HABD-mutant, or fragment, may be used for the screening. This may provide a more specific search for finding anti-angiogenic molecules.

In one embodiment, the potential binding partner is chosen from the group comprising: proteins, glycoproteins, proteoglycans, heparan sulphates, lipids, glycans, glycosides and saccharides.

In another embodiment, the potential binding partner is a receptor molecule, or a part of a receptor molecule or a molecule binding to a cell surface receptor molecule or a molecule located at the cell surface without being a receptor molecule.

In yet another embodiment, the potential binding partner is an extracellular molecule, being localized in the extracellular matrix, tissue sinuses, lymph- or blood vessels.

In yet another aspect, the invention relates to a binding partner for a molecule comprising the CD44HABD found by the method described above. The said binding partner, being a molecule promoting or inhibiting angiogenesis and therefore a potential target for the development of novel inhibitors of angiogenesis, e.g. a cell surface receptor that normally confers pro-angiogenic signaling, including a receptor for soluble angiogenic factors, such as growth factor receptor (e.g. VEGF-receptor family, FGF-receptor family, EGF-receptor family, PDGF-receptor family), receptor for the extracellular matrix (e.g. integrins, syndecans, proteoglycans), cell-cell-adhesion receptor (e.g. Cadherins, Ig-like superfamily, selectins). The receptor transduces pro-angiogenic signals into endothelial cells or block anti-angiogenic signaling or promote anti-angiogenic signaling in endothelial cells. Activation of this receptor to signal occurs by binding to an extracellular ligand or by activation targeting the cytoplasmic domain of the receptor by intracellular signaling events. Alternatively, the receptor at the cell surface acts as a carrier that transports and directs its ligand to an intracellular receptor (e.g. nuclear receptor), both which are examples of potential binding partners that may be identified by the claimed screening methods and may be utilized as anti-angiogenic targets.

In still another aspect, the invention refers to a kit for carrying out the method described above comprising, in separate vials, the molecule, or the genetic information, comprising the CD44HABD, analogues or mutants or parts thereof, and the potential binding partner, or parts thereof.

In yet another aspect the invention refers to the use of a molecule comprising the CD44HABD-, as well as analogues, recombinant and mutated variants or fragments thereof for targeting of endothelial cells. Since the CD44HABD-molecule of the invention has shown the capacity to bind endothelial cells, it may be used to target such cells.

In one embodiment, the molecule further comprises a moiety showing chemotherapeutic and gene therapy properties. Hereby, the CD44-HABD-molecule of the invention, in a modified variant, may be used as an anti-tumor drug towards endothelial cells. As the skilled person in the art realizes, the function that is coupled to the CD44-HABD-molecule of the invention may also have other properties than anti-tumoral such as anti-endothelial cell proliferation and/or migration, pro-apoptotic or disrupting essential functions of endothelial cells or other vascular cells. However, a moiety having anti-tumoral properties is one preferred embodiment.

By "showing chemotherapeutic properties" is meant that the molecule having this property has the capacity to inhibit the growth and/or kill the cells it is targeted for, as measured by use of in vitro tissue culture of cells or tissues, in vitro screening of enzymatic activity, e.g. kinase, phosphatase, glycosylation, acetylation, proteolysis, linker ligation or any other enzymatic activities, proton transfer, in vitro or in vivo screening of ion pump function, and/or in vivo or in vitro screening of cell growth, apoptosis, or other means of cell death, tumor progression, metastasis, invasion, angiogenesis and/or tissue homeostasis.

The moiety showing chemotherapeutic and/or gene therapy properties may for example be chosen from different viruses for gene therapy, various chemotherapeutics, which would be known by the skilled person of the art, naked DNA coupled to HABD, mutants, or fragments thereof, as well as other DNA-carriers, including but not limited to lipids, peptides and proteins.

For example, Arap et al. (Science, 1998, 279: 377-380), Ellerby et al. (Nature Medicine, 1999,5; 9:1032-1038), and Trepel et al. (Human Gene Therapy, 2000, 11:1971-1981) discloses the coupling of a doxorubicin molecule (cytostatica), the coupling of an apoptosis-inducing peptide, and the coupling of a virus, respectively, for targeting of endothelial cells.

The coupling of a virus is an example on how an endothelial-targeting molecule can be used for gene therapy.

Accordingly, in yet another embodiment, the invention relates to a molecule comprising the CD44HABD, as well as analogues, recombinant and mutated variants or fragments thereof, and a moiety showing chemotherapeutic and/or gene therapeutic properties.

In still another embodiment, the invention relates to a molecule of the invention coupled to a moiety having chemotherapeutic properties as defined above, for medical use.

The invention will now be described with reference to the following examples, which are intended for illustrative purposes only, and do not limit the scope of the invention in any way.

EXAMPLES

Example 1

Construction and Purification of Wild-Type and Mutant Human CD44HABD as Non-Glycosylated GST Fusion Protein Human CD44 standard isoform cDNA (Stamenkovic et al., EMBO J 1991; 10: 343-8) was used to PCR amplify the hyaluronic acid binding domain, covering amino acids 21-132 (SEQ ID NO: 2), with the oligonucleotides 5'CGC-GAATTCAGATCGATTTGAATATG 3' (SEQ ID NO: 13) (containing internal EcoR1 cleavage site) and 5'CGC-GAGCTCCTTCTAACATGTAGTCAG 3' (SEQ ID NO: 14) (containing internal Sac1 cleavage site). The resulting PCR amplification product was cloned into a pGEX-KG vector (Guan and Dixon, Anal Biochem 1991; 192: 262-7). Generation of CD44HABD hyaluronic acid non-binding mutant was performed by site-directed mutagenesis according to the manufacurer's protocol (Quickchange.RTM., Stratagene). Mutagenic oligo pairs:

```
For R41A
                                    (SEQ ID NO: 15)
  (5'GAGAAAAATGGTGCCTACAGCATCTCTCGG-3'
  and (SEQ ID NO: 16)
  5'AGATGCTGTAGGCACCATTTTTCTCCACG-3', For R78SY79S
                                    (SEQ ID NO: 17)
  (5'GACCTGCAGCTCTGGGTTCATAG 3',
  and (SEQ ID NO: 18)
  5'ATGAACCCAGAGCTGCAGGTCTC 3'
``` were used for introduction of R41A and R78S, Y79S mutations respectively into wild type CD44HABD.

Chicken CAM and dog liver RNA were purified from the respective tissues using RNAqueous kit from Ambion (Austin Tex.) according to manufacturers specifications. CDNAs encoding chicken and dog CD44HABD were obtained by RT-PCR with primers specific to nucleotides 63-81 (SEQ ID NO: 4) and 359-330 (SEQ ID NO:6) of CD44 from the respective species. The primer pairs were as follows:

```
For chicken:
5'-CAGAGACACAATTCAATATA-3',   (SEQ ID NO: 19)
and

5'-TTGGCTCACATGCTTTG-3'       (SEQ ID NO: 20)

Fr dog:
5'-CGCAGATCGATTTGAACATA-3',   (SEQ ID NO: 21)
and

5'-CCGATGTACAATCCTCTTC-3'.    (SEQ ID NO: 22)
```

Figure 1:
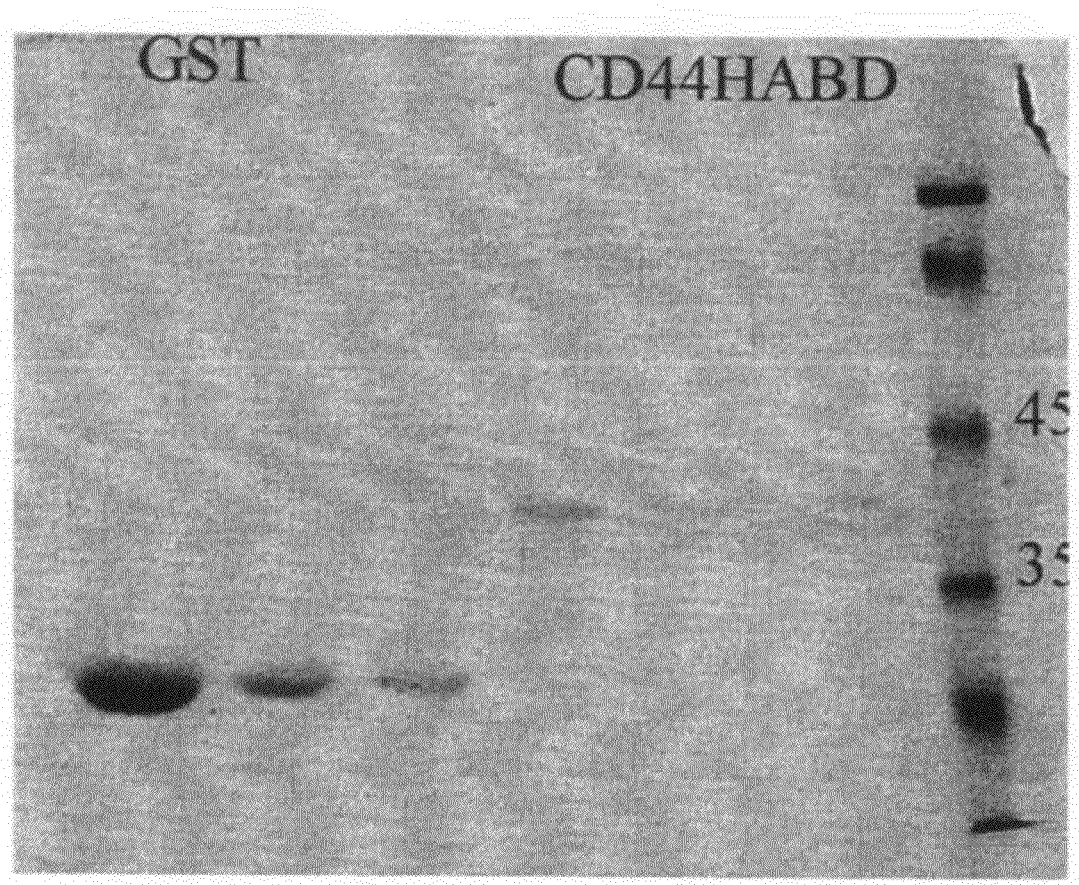

The cDNAs corresponding to SEQ ID NO: 3 (dog) and SEQ ID NO: 5 (chicken) were cloned into bacterial expression vector pET15b (Novagen) that expresses proteins in *E. coli* as fusions with His-tag. Wild type and R41A, R78S, Y79S mutant GST-CD44HABD expression was induced in *E. coli* BL21 strain at 27° C. with 1 mM IPTG at $OD_{600}$=0.7 and purified using glutathione agarose beads (Sigma) according to manufacture's protocol. The resulting protein was essentially pure as detected by Coomassie Brilliant Blue staining of the preparation separated by SDS polyacrylamide electrophoresis (FIG. 1). Chicken and dog CD44HABD were purified using the HICAM Resin (Sigma) according to manufacturer's protocol. The resulting protein was also essentially pure and free of contaminants as judged by Coomassie Brilliant Blue staining of SDS-polyacrylamide gels.

As is indicated already above, bacterially expressed proteins lack any posttranslational modifications and accordingly the putative N-linked glycosylation sites of CD44HABD are non-glycosylated in the recombinant protein as produced under this example and used in all the following examples.

Example 2

Figure 2:
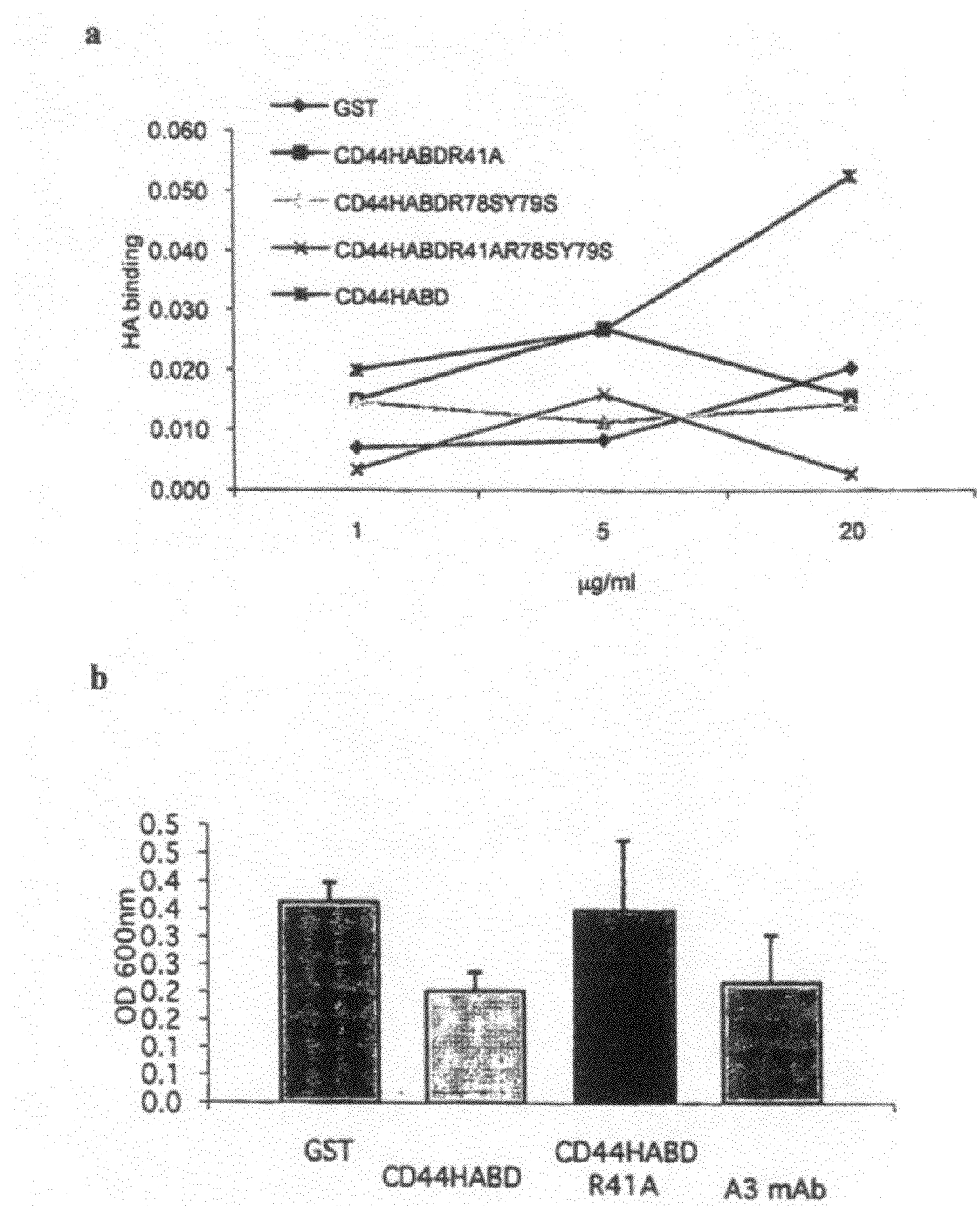
FIG. 2 shows that recombinant CD44HABD binds to hyaluronic acid. a, wild type CD44HABD, but not R41A, R78SY79S or R41AR78SY79S HA non-binding mutants, binds to immobilized HA. b, CD44HABD inhibits human aortic endothelial cell migration towards HA, whereas R41A HA-non-binding mutant has no effect. A3, monoclonal antibody to CD44, that blocks HA binding, and also inhibit endothelial cell migration.
Figure 3A:
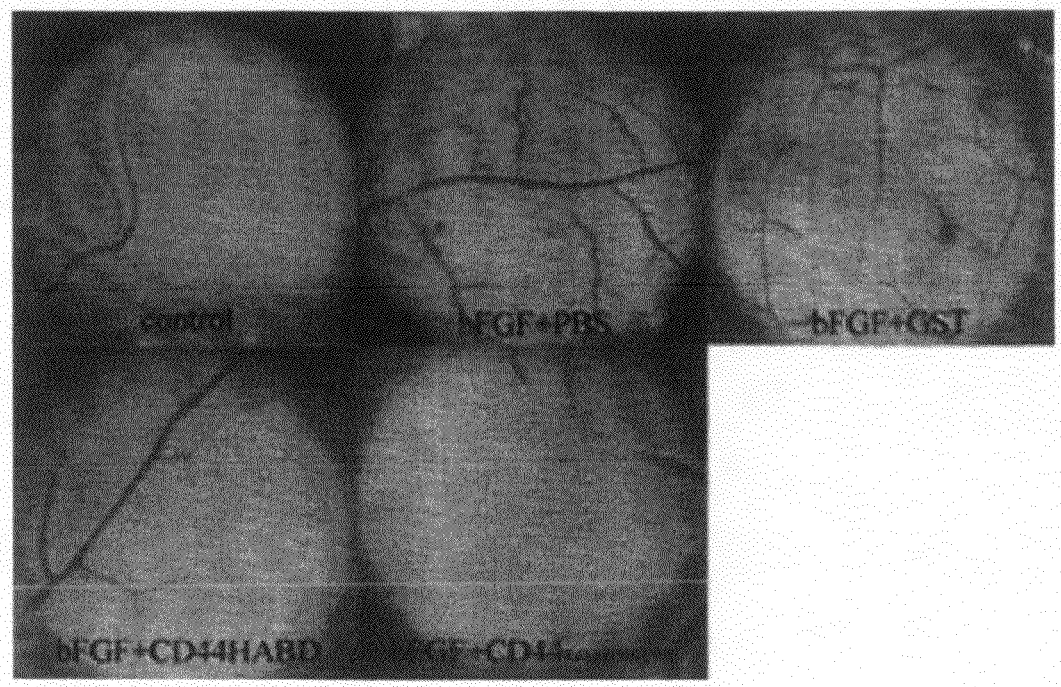
FIG. 3 shows that recombinant human CD44HABD blocks angiogenesis in vivo in chick chorio-allantoic membrane. a, Filter discs and associated CAM from typical angiogenesis experiment where angiogenesis was induced with bFGF. b-d, Angiogenesis was assessed as number of blood vessel branch points; mean angiogenic index+/−SEM. *($P<0.05$), significant results.

Recombinant Wild-Type but not Mutant CD44HABD can Bind Hyaluronic Acid (HA) in Dose-Dependent manner and can Inhibit Haptotaxis of Human Aortic Endothelial Cells (HAEC) Towards HA High molecular weight hyaluronic acid at 1 mg ml$^{-1}$ (Sigma) in PBS was used to coat Maxisorp (Nunc) plates overnight at room temperature (RT). Wells were washed with PBS and blocked with 2% BSA for 2 h at RT. Purified proteins diluted in PBS were added to the wells and incubated 1 h at RT. After three times washing with PBS-T, mouse anti GST antibody B-14 (Santa Cruz Biotechnology) was incubated 1 h at RT before further washing and 1 h incubation at RT with HRP-conjugated goat anti mouse secondary antibody (Dako). HA binding was visualized by with OPD chromogenic substrate (Sigma) and absorbance was read at 450 nm. As shown in FIG. 2A, wild type but not mutant CD44 fusion proteins bind HA in a concentration dependent manner.

Human aortic endothelial cells (HAEC) were obtained from Clonetics and grown in EBM-2 media (Clonetics) supplemented with 10% FCS, 2 μg ml$^{-1}$ mouse EGF (Sigma) and 50 μg ml$^{-1}$ gentamycin. Cell migration assay was performed in Transwell migration chambers (pore size 8 mm; Costar). Lower compartment of chambers contained 1 μg ml$^{-1}$ high molecular weight hyaluronic acid (Sigma). CD44HABD, CD44HABD$^{R41A}$ or GST (10 μg ml$^{-1}$) was added to the lower compartment. For antibody inhibition assay, cells were preincubated 30 min with 10 μg ml$^{-1}$ anti CD44 mAb A3 (Guo et al., 1993, 1994). Aortic endothelial cells were added to the upper compartment of the Transwell chamber and allowed to migrate to the underside of the membrane for 2.5 h. The migrated cells were fixed and stained with 0.5% crystal violet. After washing membranes were dried and bound dye was eluted with 10% acetic acid. Optical density of recovered elute was spectrophotometrically read at 600 nm. The results shown in FIG. 2B demonstrate that wild type CD44HABD but not respective non-HA-binding R41A mutant, inhibited human aortic endothelial cell migration towards HA whereas migration was also inhibited by antibody that specifically blocks CD44 binding to HA (A3).

Example 3

Recombinant CD44 Fusion Proteins Block Angiogenesis in Chick Cam Independent on HA-Binding 10-day-old chick embryos were prepared as described in [Brooks et al., J Clin Invest 1995; 96: 1815-22]. For angiogenesis assay, filter discs soaked with 100 ng ml$^{-1}$ VEGF (Sigma), 100 ng ml$^{-1}$ TGFα (Sigma) or 1 μg ml$^{-1}$ bFGF (Gibco Lifetech) were placed on CAMs, followed by daily ectopical addition of 10 μg of CD44HABD, CD44HABD$^{R41AR78SY79S}$ or GST and PBS as controls (n=6 per group). After 72 h, filter discs and the surrounding CAM tissue were dissected and angiogenesis quantified in a dissection microscope. Angiogenesis was assessed as the number of blood vessel branch points within the CAM area directly under the filter discs.

GST-CD44HABD and GST-CD44HABD$^{R41AR78SY79S}$ but not GST treatment completely abolished the angiogenic effect of VEGF, bFGF or TGFα (FIG. 3a-d), indicating that soluble CD44HABD blocks angiogenesis induced by three distinct angiogenic factors and this inhibition is independent on HA binding since HA non-binding mutants were equally effective in inhibiting angiogenesis.

Example 4

Figure 4:
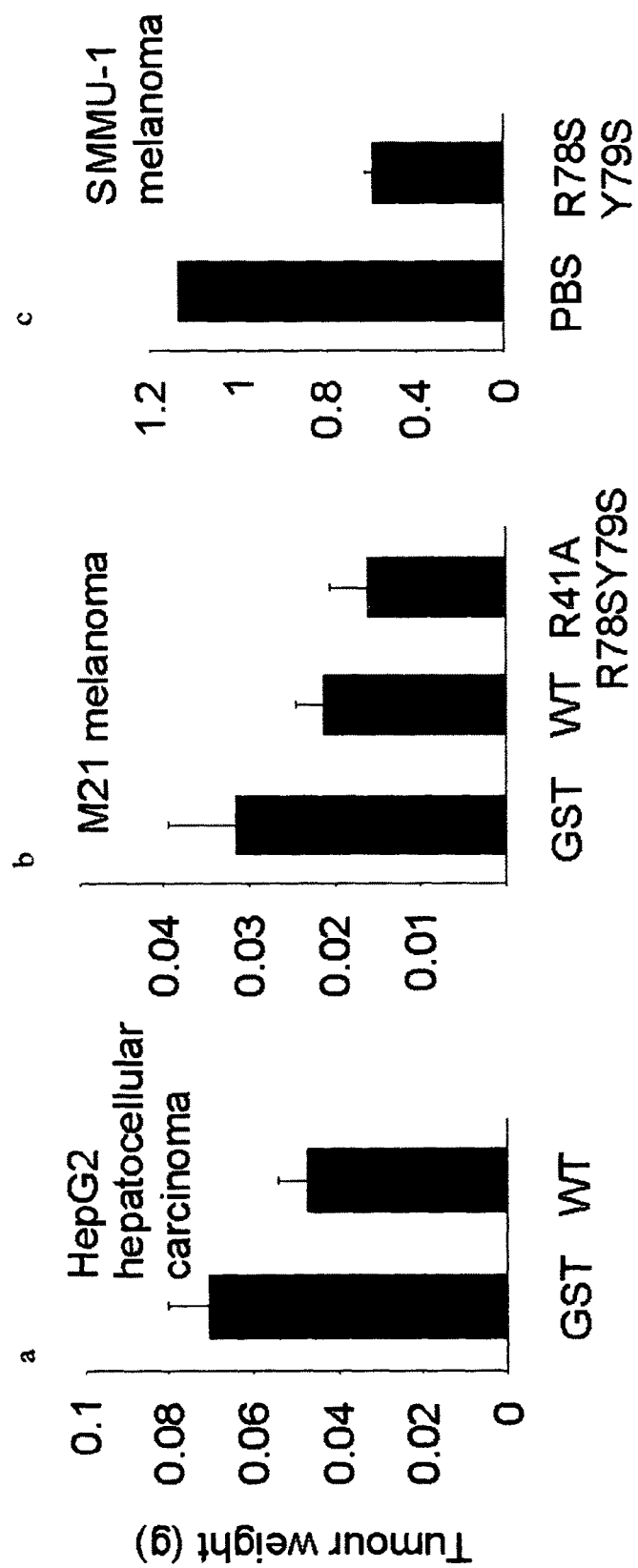
FIG. 4 shows that recombinant CD44HABD inhibits melanoma (SMMU-1, M21) and hepatocellular carcinoma (HepG2) growth in chick CAM.

Recombinant CD44HABD Proteins Block the Growth of Different Tumor Cell Lines on Chick Cam Independent of HA-Binding Capacity SMMU-1 human melanoma cells were originally isolated from primary tumor and is CD44-negative (Guo et al., Cancer Res 1994; 54: 1561-5). HepG2 human hepato-cellular carcinoma was grown in RPMI1640 containing 10% fetal bovine serum and 50 mg ml$^{-1}$ ginomycin. SMMU-1-cells and M21 cells were grown in DMEM containing 10% fetal bovine serum and 50 μg ml$^{-1}$ gentamycin. The cells were detached from the plates by trypsinization and 1 million cells were seeded onto the CAMS of 10-day old chicken embryos. The tumors were treated every two days with 10 μg of the fusion protein of either human or chicken origin in 100 μl of PBS or with vehicle alone. 7 days later the tumors were resected and the wet mass was determined. As shown in FIG. 4 the tumor growth of all tested tumor cell lines was inhibited significantly by HA-binding wild type as well as by HA-nonbinding mutated CD44HADB.

Example 5

Recombinant CD44 Fusion Proteins Inhibit Tumor Growth in Nude Mice Independent of HA-Binding Capacity 1×10$^6$ SMMU-1 cells were injected subcutaneously into backs of 6-week old female BALB/cABom nude mice (M&B). Next day mice were injected subcutaneously proximal to the tumor with 2.4 mg kg$^{-1}$ of body weight of GST-CD44HABD, GST-CD44HABD$^{R41AR78SY79S}$ or GST alone in 100 μl PBS. The treatment was repeated every second day and animals were sacrificed after two weeks, tumors dissected and analyzed for weight and prepared for tissue analysis. Subcutaneous treatment of mice with CD44HABD or non-HA-binding mutant CD44HABD$^{R41AR78SY79S}$ significantly reduced tumor growth when compared to GST-treated controls (FIG. 5a, c, P<0.05 at all time points). At day 16, when mice were sacrificed, CD44HABD and CD44HABD$^{R41AR78SY79S}$ treated mice had in average 45% smaller tumor burden (47% and 43% respectively) than GST-treated mice (FIG. 5b).

For immunohistochemical analysis, 4 μm thick tissue sections were cut from formalin fixed and paraffin embedded SMMU-1 tumors of similar size. Blood vessel staining on tissue sections was performed using goat anti-mouse PECAM-1 (Santa Cruz Biotech) primary antibody and primary antibody binding was detected by alkaline phosphatase conjugated anti-goat secondary antibodies and developed using Vectastain kit (Vector Laboratories). Immunohistochemical analysis of tumors by staining for PECAM-1 positive blood vessels showed that CD44HABD and CD44HABD$^{R41AR78SY79}$ treated tumors were also less vascularized at the tumor border (FIG. 5d).

Example 6

Recombinant Non-Glycosylated CD44HABD$^{R41AR78SY79}$ (CD44-3MUT) Affects on Xenografted Human Tumors Hep3b cells (3.5×10$^6$) were injected subcutaneously into Foxn1 athymic nude mice. Intraperitoneal treatment with drugs started on day 14 post inoculation when the average tumor volume reached 150 mm$^3$. Administration of 10 μg of CD44-3MUT 3 times a week decreases tumor growth significantly. Results on are shown in FIG. 9. (FIG. 1 OF THE REPORT) Administration of CD44-3MUT in the range of 2-50 μg/mouse (0.1-2.5 mg/kg) inhibits tumor growth in dose-dependent manner.

We have also shown that CD44-3MUT effect on tumor growth is dose-dependent regardless of the method of administration. FIG. 9 shows the results when the protein was administered intraperitoneal but there were no significant differences when the administration was intravenous (results not shown).

Taken into account that CD44-3MUT is a protein of small size that has relatively short clearance kinetics we have also used constant drug administration using intraperitoneal micro-osmotic pumps over the period of 14 days. Such administration routine gives consistent level of CD44-3MUT and might improve the anti-angiogenic and anti-tumour efficacy. We have shown that CD44-3MUT administrated using micro-osmotic pump giving the dose of 1 μg/mouse/day inhibits tumor growth significantly and more effectively than the same dose administrated intraperitoneally (FIG. 10).

Example 7

CD44HABD$^{R41AR78SY79}$ (CD44-3MUT) Affects the Growth of Blood Vessels as Tested in Ex Vivo Chick Aortic Assay The inhibitory effect of CD44-3MUT to the growth of blood vessels was confirmed also in ex vivo chick aortic ring assay. Results are shown in FIG. 11. In this system, aortic rings cultured in collagen gel give rise to micro vascular networks composed of branching endothelial channels. By using intact vascular explants, it reproduces more accurately the environment in which angiogenesis takes place than those with isolated endothelial cells. The growth of blood vessels from chicken embryo aortic ring embedded into collagen-I gel was induced by VEGF according to the used method (Auerbach et al., 2003; Clinical Chem. 49:1; 32-40) and test proteins were added directly into the growth matrix. Significant reduction of VEGF induced angiogenesis after CD44-3MUT treatment was observed.

Example 8

CD44-HABD Fusion Proteins Inhibit the Growth of Human Pancreatic Cancer also in Nude Mice Independent of HA-Binding Capacity 1×10$^6$ BxPC-3 (ATCC, Manassas, Va.) cells were injected subcutaneously into backs of 6-8 week old female BALB/cABom nude mice (M&B, Ry, Denmark). When tumor nodules appeared mice started to receive by subcutaneous injections proximal to the tumor 20 μg (BxPC-3) or 50 μg (SMMU-1) of GST-CD44HABD, GST-CD44HABD$^{R41AR78SY79S}$ or GST in 100 μl PBS. The treatment was repeated in every second day and animals were sacrificed when most of control tumors reached 25 mm in diameter. Tumor volume was calculated using formula (Width$^2$×Length)×0.52. At the end of experiment tumors were dissected out, analyzed for weight and prepared for tissue analysis. BxPC-3 cells gave rise to slowly growing tumors. The GST-treated controls reached the average weight of 0.267+/−0.042 g at day 52 when mice were sacrificed (FIG. 2d-g). The treatment of mice with GST-CD44HABD or GST-CD44HABD$^{R41AR78SY79S}$ significantly inhibited BxPC-3 tumor growth reducing the average tumor weight by 60% (0.108+/−0.028 g) and 70% (0.085+/−0.017 g) compared to control, respectively (P<0.05; n=6). Results are shown in FIG. 6.

Example 9

CD44-3MUT Treatment is as Efficient as Anti-VEGF Therapy

We have also compared the effects of CD44-3MUT and anti-VEGF antibody (Avastin, bevacizumab, Roche). Avastin is an approved angiogenesis inhibitor. It is, in combination with intravenous 5-fluorouracil-based chemotherapy, indicated for first- or second-line treatment of patients with metastatic carcinoma of the colon or rectum. In combination with carboplatin and paclitaxel, is indicated for first-line treatment of patients with unrespectable, locally advanced, recurrent or metastatic non-squamous, non-small cell lung cancer. In combination with paclitaxel Avastin is indicated for the treatment of patients who have not received chemotherapy for metastatic HER2-negative breast cancer.

It has been shown in animal model that Avastin inhibits grafted human tumor growth in mice also as a monotherapy. We compared Avastin efficacy with efficacy of CD44-3MUT. The experimental conditions were similar to those shown in Example 6. As is shown in FIG. 12 CD44-3MUT treatment gives similar effect compared to anti-VEGF therapy.

Example 9

Recombinant CD44HABD Inhibits Specifically Endothelial Cell Proliferation In Vitro and Blocks Endothelial Cell Cycle For cell cycle analysis exponentially growing primary human vascular endothelial cells (HUVEC), cow pulmonary arterial endothelial (CPAE) cells, primary human fibroblasts (NHDF), MCF-7 or SMMU1 cells were incubated 48 h in the presence of 30 μg ml$^{-1}$ GST-CD44HABD, GST-CD44HABD$^{R41AR78SY79-S}$, GST or PBS. Cells were pulsed with 30 μg ml$^{-1}$ bromodeoxyuridine (BrdU) for 60 min, harvested and fixed in ice-cold ethanol. Cells were then stained for BrdU with anti-BrdU mAb G3G4 (Developmental Studies Hybridoma Bank, University of Iowa, Iowa) diluted 1:50 followed by fluorescein isothiocyanate-conjugated goat anti-mouse antibody (Jackson Immunoresearch, West Grove, Pa.) in parallel with staining with propidium iodide. The cell cycle distribution was then analyzed with a FACScan Flow Cytometer (Becton Dickinson, Franklin Lakes, N.J.).

Human vascular endothelial cells and cow pulmonary arterial endothelial cells exposed to GST-CD44HABD or GST-CD44HABD$^{R41AR78SY79-S}$ displayed a markedly reduced amount of cells in S-phase (5% and 6%, respectively) as compared to control treated cells (25%; FIG. 7D). Furthermore, CD44HABD had no significant effect on the cell cycle of primary human fibroblasts (NHDF) or on any of the tumor cells tested, suggesting that cell cycle inhibition by CD44HABD is specific for endothelial cells.

Example 10

Characterization of CD44-3MUT (CD44HABD$^{R41AR78SY79S}$)

We tested cellular binding of CD44-3MUT on different endothelial, lymphoid and tumor cell lines to characterize it's cell-type specificity and to obtain an estimate of it's equilibrium dissociation constant (Kd) and maximum number of binding sites (Bmax).

For binding assays we used Hep3B human hepatocellular carcinoma, MCF-7 human breast adenocarcinoma, COS-1 African green monkey kidney fibroblasts, cow pulmonary artery endothelial cells (CPAE), human umbilical vein endothelial cells (HUVEC), RAMOS and RAJI human Burkitt's lymphoma cells, and THP-1 human monocytic leukemia cell lines. Saturation binding experiments were done by incubating cells with different concentrations of 125I-labeled CD44-3MUT. Nonspecific binding was defined by the addition of excess nonradioactive CD44-3MUT into reaction. To test whether cellular binding of CD44-3MUT is mediated via hyaluronic acid, we treated cells in some experiments with hyaluronidase to destroy possible binding sites. Bound radioactivity was quantified using γ-counter. Specific and nonspecific binding was analyzed using simultaneous nonlinear curve fitting function in GraphPad Prism 4/5 software.

We found that HUVEC binds 125I-CD44-3MUT with average Kd 146±72 nM and Bmax 0.028±0.019 fmol/cell (n=15; mean±SD). Ramos lymphoma cells bound 125I-CD44-3MUT with average Kd 54±22 nM (FIG. 13A, Table 1). We tested also wild type 125I-CD44-HABD binding to HUVEC treated with hyaluronidase or left untreated. 125I-CD44-HABD bound to HUVEC with average Kd 82±28 nM (n=3) (FIG. 13B,C). Whereas hyaluronidase treatment of HUVEC had no significant effect on 125I-CD44-3MUT binding yielding Kd 188±38 nM and Bmax 0.039±0.022 fmol/cell (n=4) (FIGS. 13B and C). Interestingly, CD44-3MUT has up to 10 times more binding sites on HUVEC than wt CD44-HABD.

TABLE 1

125I-CD44-3MUT cellular binding

|  | Kd, nM | Bmax, fmol/cell | n[b] | cells origin |
| --- | --- | --- | --- | --- |
| Ramos | 54 ± 22[a] | 0.0198 ± 0.0054 | 2 | Burkitt's lymphoma cells |
| Raji | 140 ± 9 | 0.0175 ± 6.2E−05 | 2 | Burkitt's lymphoma cells |
| THP-1 | 93 ± 19 | 0.0226 ± 0.0133 | 5 | human myelocytic leukemia |
| HUVEC | 146 ± 72 | 0.028 ± 0.019 | 15 | human umbilical vein endithelial cells |
| PC-3 | 171 ± 62 | 0.0192 ± 0.0023 | 2 | human prostate adenocarcinoma |
| COS-1 | 176 ± 74 | 0.0305 ± 0.021 | 5 | green monkey kidney fibroblasts |
| CPAE | 185 | 0.08 | 1 | cow pulmonary artery endothelial cells |
| MCF-7 | 422 ± 379 | 0.095 ± 0.097 | 2 | human breast adenocarcinoma |
| Hep3B | 966 ± 764 | 0.265 ± 0.19 | 4 | human hepatocellular carcinoma |

[a]values shown as mean ± SD.
[b]number of experiments

In addition to HUVEC and Ramos, 125I-CD44-SMUT binds with comparable affinity to other tested cell lines including Raji lymphoma, THP-1 monocytic leukemia, PC-3 prostate carcinoma, COS-1 monkey fibroblasts and CPAE cow aortic endothelial cells (Table 1). Binding to MCF-7 breast carcinoma cells is saturable but with lower affinity, Kd 422±379 nM. 125I-CD44-3MUT binding to Hep3B hepatic carcinoma remained virtually unsaturated.

These results suggest that there is a specific binding site for CD44-3MUT protein on the surface of cells of different origin.

Example 11

CD44-3MUT Does not Bind to VEGF Receptors In Vitro

Results of Example 3 above, show that CD44-3MUT inhibits angiogenesis induced by different growth factors (TGF-alfa, bFGF and VEGF) in chick CAM, suggesting the CD44-3MUT target in angiogenesis inhibition is downstream of these signaling pathways, i.e. CD44-3MUT is not blocking growth factor binding to their receptors. To test the hypothesis we directly measured CD44-3MUT binding to VEGF receptors. VEGF signaling pathway is a well exploited mechanism targeted by many different anti-cancer drugs (e.g. Avastin). We have developed a modified ELISA test (to detect CD44-3MUT binding specificity to isolated recombinant receptors VEGFR1 and VEGFR2). Obtained results indicate that CD44-3MUT does not bind to VEGF receptors in vitro, as does VEGF itself in our assay (FIG. 14) Therefore the anti-angiogenic effect of CD44-3MUT is most probably not due to direct interference with VEFG-related signal transduction.

Example 12

CD44-3MUT Binds to Activated/Growth Factor Induced Endothelial Cells

Next we examined whether the activation of endothelial cells by VEGF has effect on CD44-3MUT cellular binding. For this, we serum starved HUVEC for 6 h followed by indction with 10 ng/ml VEGF for 30 min. After induction HUVEC were incubated with fluorescence-labeled CD44-3MUT at 4 C. Results show that treatment of endothelial cells with VEGF increases significantly CD44-3MUT bound HUVEC-cells from 26.8%-6.1 to 38%=/−7.9 (P=0.028, two tailed paired t-test, FIG. 15). This experiment shows that CD44-3MUT binds preferably to activated/growth factor induced endothelial cells, indicating that in physiological context CD44-3MUT will be probably targeted to sites where endothelial cell proliferation and/or migration takes place or where endothelial permeability is changed (e.g. angiogenesis, wound healing, inflammation).

Example 13

CD44-3MUT Inhibits Endothelial Cell Proliferation in a Dose-Dependent Fashion

Exponentially growing HUVE cell populations were treated with respective proteins for 24 h. Cells were double-stained with propidium iodide and BrdU and analyzed by FACS. Results showing that CD44-3MUT treatment inhibits endothelial cell proliferation in a dose-responsive way are depicted in FIG. 16.

What is claimed is:

1. A method for treating states related to the inhibition of angiogenesis and/or endothelial cell proliferation, the method consisting the steps of:
   a. expressing non-HA binding variant of CD44-hyaluronic acid binding domain in bacterial cells;
   b. purifying the resulting non-glycosylated protein;
   c. administering the purified non-glycosylated non-HA-binding variant of CD44-hyaluronic acid binding domain (CD44-HABD) to a patient.

2. The method according to claim 1, wherein the non-HA binding variant of CD44-HABD has an amino acid sequence selected from the group consisting of SEQ ID NO: 8, SEQ ID NO:10 and SEQ ID NO:12.

3. The method according to claim 1, wherein the non-HA-binding variant of CD44-hyaluronic acid binding domain (CD44-HABD) is further connected to a fusion protein partner part.

4. The method of claim 1, wherein the state to be treated is selected from the group consisting of ocular diseases causing blindness or impaired vision, states of chronic inflammation, psoriasis, atherosclerosis, restenosis, cancer growth and metastasis, all forms of cancer diseases and tumors and hemangioma.

5. A method to target endothelial cells by providing a molecule comprising a non-HA binding variant of CD44-hyaluronic acid binding domain expressed in bacterial cells.

6. The method according to claim 5, wherein the non-HA binding variant of CD44-HABD has an amino acid sequence selected from the group consisting of SEQ ID NO: 8, SEQ ID NO:10 and SEQ ID NO:12.

7. The method according to claim 6, wherein the molecule further comprises a moiety having chemotherapeutical and/or gene therapeutic properties.

8. The method of claim 1, wherein the mode of action of the non-HA-binding variant of CD44-hyaluronic acid binding domain (CD44-HABD) is independent of hyaluronic acid.

9. The method of claim 5, wherein endothelial cell proliferation is inhibited.

10. The method of claim 1, wherein tumor growth is inhibited.

11. The method of claim 1, wherein effective amount of the non-HA-binding variant of CD44-hyaluronic acid binding domain is 0.1 -2.5 mg/kg.

12. The method of claim 1, wherein the molecule is administered orally or parentally.

13. The method of claim 1, wherein the bacterial cell is *E.coli*.

14. The method of claim 5, wherein the bacterial cell is *E.coli*.

* * * * *

SEQUENCE LISTING

<160> NUMBER OF SEQ ID NOS: 24

<210> SEQ ID NO 1
<211> LENGTH: 336
<212> TYPE: DNA
<213> ORGANISM: Homo sapiens

<400> SEQUENCE: 1
cagatcgatt tgaatataac ctgccgcttt gcaggtgtat tccacgtgga gaaaaatggt      60
cgctacagca tctctcggac ggaggccgct gacctctgca aggctttcaa tagcaccttg     120
cccacaatgg cccagatgga gaaagctctg agcatcggat ttgagacctg caggtatggg     180
ttcatagaag gcatgtggt gattccccgg atccacccca actccatctg tgcagcaaac      240
aacacagggg tgtacatcct cacatacaac acctcccagt atgacacata ttgcttcaat     300
gcttcagctc cacctgaaga agattgtaca tcagtc                                336

<210> SEQ ID NO 2
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: CD44 HABD

<400> SEQUENCE: 2

Gly Ile Asp Leu Asn Met Thr Cys Arg Phe Ala Gly Val Phe His Val
1               5                   10                  15

Glu Lys Asn Gly Arg Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Arg Tyr Gly Phe Ile Glu Gly
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

<210> SEQ ID NO 3
<211> LENGTH: 336
<212> TYPE: DNA
<213> ORGANISM: Canis familiaris

<400> SEQUENCE: 3
cgcagatcga tttgaacata acctgccgct acgcaggtgt gttccatgtg agaaaaacg      60 gtcgctacag catctccagg acggcggctg ccgacctctg caaggctttc aacagcaccc    120
tgcccaccat ggcccagatg gagcgagccc tgagcgtggg ctttgagacc tgcaggtacg    180
ggttcataga aggacatgtg gtgatccccc gtatccaacc caatgctatt tgtgctgcaa    240
accatacagg ggtgtacatc ctcatatcca acacctccca gtacgacacg tattgcttca    300
atgcttcagc tccacctgaa gaggattgta catcgg                               336

<210> SEQ ID NO 4
<211> LENGTH: 112

```
<212> TYPE: PRT
<213> ORGANISM: Canis familiaris
<220> FEATURE:
<221> NAME/KEY: PEPTIDE
<222> LOCATION: (1)..(112)
<223> OTHER INFORMATION: CD44 HABD

<400> SEQUENCE: 4

Gln Ile Asp Leu Asn Ile Thr Cys Arg Tyr Ala Gly Val Phe His Val
1               5                   10                  15

Glu Lys Asn Gly Arg Tyr Ser Ile Ser Arg Thr Ala Ala Ala Asp Leu
            20                  25                  30

Cys Lys Ala Phe Asn Ser Thr Leu Pro Thr Met Ala Gln Met Glu Arg
        35                  40                  45

Ala Leu Ser Val Gly Phe Glu Thr Cys Arg Tyr Gly Phe Ile Glu Gly
    50                  55                  60

His Val Val Ile Pro Arg Ile Gln Pro Asn Ala Ile Cys Ala Ala Asn
65                  70                  75                  80

His Thr Gly Val Tyr Ile Leu Ile Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

<210> SEQ ID NO 5
<211> LENGTH: 339
<212> TYPE: DNA
<213> ORGANISM: gallus gallus

<400> SEQUENCE: 5
cagagacaca attcaatata acttgcagat atggaggagt gtttcatgtg gagaaaaatg     60
gtcgctacag tctcacacga gctgaagcaa ttgagctctg tagagctctc aatagtacct    120
tggcaacact ggagcaattt gaaagagctc atgcacttgg atttgaaacg tgcaggtatg    180
gttttatagt ggggcatatt gttatcccac gaatcaatcc atatcatctt tgtgcagcaa    240
atcatacagg catttacaaa ctttcagcaa atacaactgg ccggtatgat gcatattgtt    300
acaatgcaac agaaacgagg agcaaagcat gtgagccaa                          339

<210> SEQ ID NO 6
<211> LENGTH: 112
<212> TYPE: PRT
<213> ORGANISM: Gallus gallus
<220> FEATURE:
<221> NAME/KEY: PEPTIDE
<222> LOCATION: (1)..(112)
<223> OTHER INFORMATION: CD44HABD

<400> SEQUENCE: 6

Glu Thr Gln Phe Asn Ile Thr Cys Arg Tyr Gly Gly Val Phe His Val
1               5                   10                  15

Glu Lys Asn Gly Arg Tyr Ser Leu Thr Arg Ala Glu Ala Ile Glu Leu
            20                  25                  30

Cys Arg Ala Leu Asn Ser Thr Leu Ala Thr Leu Val Gln Phe Glu Arg
        35                  40                  45

Ala His Ala Leu Gly Phe Glu Thr Cys Arg Tyr Gly Phe Ile Val Gly
    50                  55                  60

His Ile Val Ile Pro Arg Ile Asn Pro Tyr His Leu Cys Ala Ala Asn
65                  70                  75                  80

His Thr Gly Ile Tyr Lys Leu Ser Ala Asn Thr Thr Gly Arg Tyr Asp
                85                  90                  95
```

Ala Tyr Cys Tyr Asn Ala Thr Glu Thr Arg Ser Lys Ala Cys Glu Pro
            100                 105                 110

<210> SEQ ID NO 7
<211> LENGTH: 336
<212> TYPE: DNA
<213> ORGANISM: Homo sapiens

<400> SEQUENCE: 7
cagatcgatt tgaatataac ctgccgcttt gcaggtgtat tccacgtgga gaaaaatggt      60
gcctacagca tctctcggac ggaggccgct gacctctgca aggctttcaa tagcaccttg     120
cccacaatgg cccagatgga gaaagctctg agcatcggat tgagacctg caggtatggg     180 ttcatagaag ggcatgtggt gattccccgg atccacccca actccatctg tgcagcaaac     240
aacacagggg tgtacatcct cacatacaac acctcccagt atgacacata ttgcttcaat     300
gcttcagctc cacctgaaga agattgtaca tcagtc                                336

<210> SEQ ID NO 8
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: CD44 HABD mutant

<400> SEQUENCE: 8

Gln Ile Asp Leu Asn Met Thr Cys Arg Phe Ala Gly Val Phe His Val
1               5                   10                  15

Glu Lys Asn Gly Ala Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Arg Tyr Gly Phe Ile Glu Gly
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

<210> SEQ ID NO 9
<211> LENGTH: 336
<212> TYPE: DNA
<213> ORGANISM: homo sapiens

<400> SEQUENCE: 9
cagatcgatt tgaatataac ctgccgcttt gcaggtgtat tccacgtgga gaaaaatggt      60
cgctacagca tctctcggac ggaggccgct gacctctgca aggctttcaa tagcaccttg     120
cccacaatgg cccagatgga gaaagctctg agcatcggat tgagacctg cagctctggg     180 ttcatagaag ggcatgtggt gattccccgg atccacccca actccatctg tgcagcaaac     240
aacacagggg tgtacatcct cacatacaac acctcccagt atgacacata ttgcttcaat     300
gcttcagctc cacctgaaga agattgtaca tcagtc                                336

<210> SEQ ID NO 10
<211> LENGTH: 112
<212> TYPE: PRT

```
<213> ORGANISM: Homo sapiens
<220> FEATURE:
<221> NAME/KEY: PEPTIDE
<222> LOCATION: (1)..(112)
<223> OTHER INFORMATION: CD44 HABD mutant

<400> SEQUENCE: 10

Gln Ile Asp Leu Asn Met Thr Cys Arg Phe Ala Gly Val Phe His Val
1               5                   10                  15

Glu Lys Asn Gly Arg Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Ser Ser Gly Phe Ile Glu Gly
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
            100                 105                 110

<210> SEQ ID NO 11
<211> LENGTH: 336
<212> TYPE: DNA
<213> ORGANISM: Homo sapiens

<400> SEQUENCE: 11
cagatcgatt tgaatataac ctgccgcttt gcaggtgtat tccacgtgga gaaaaatggt      60
gcctacagca tctctcggac ggaggccgct gacctctgca aggctttcaa tagcaccttg     120
cccacaatgg cccagatgga gaaagctctg agcatcggat ttgagacctg cagctctggg     180
ttcatagaag gcatgtggt gattccccgg atccacccca actccatctg tgcagcaaac      240
aacacagggg tgtacatcct cacatacaac acctcccagt atgacacata ttgcttcaat     300
gcttcagctc cacctgaaga agattgtaca tcagtc                               336

<210> SEQ ID NO 12
<211> LENGTH: 112
<212> TYPE: PRT
<213> ORGANISM: Homo sapiens
<220> FEATURE:
<221> NAME/KEY: PEPTIDE
<222> LOCATION: (1)..(112)
<223> OTHER INFORMATION: CD44 3-MUT

<400> SEQUENCE: 12

Gln Ile Asp Leu Asn Met Thr Cys Arg Phe Ala Gly Val Phe His Val
1               5                   10                  15

Glu Lys Asn Gly Ala Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Ser Ser Gly Phe Ile Glu Gly
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Ala Pro Pro Glu Glu Asp Cys Thr Ser Val
```

<210> SEQ ID NO 13
<211> LENGTH: 27
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(27)
<223> OTHER INFORMATION: primer

<400> SEQUENCE: 13
cgcgaattcc agatcgattt gaatatg                27

<210> SEQ ID NO 14
<211> LENGTH: 27
<212> TYPE: DNA
<213> ORGANISM: artificial
<220> FEATURE:
<223> OTHER INFORMATION: chemically synthesized
<220> FEATURE:
<221> NAME/KEY: CDS
<222> LOCATION: (1)..(27)
<223> OTHER INFORMATION: primer

<400> SEQUENCE: 14 cgc gag ctc ctt cta aca tgt agt cag                27
Arg Glu Leu Leu Leu Thr Cys Ser Gln
1               5

<210> SEQ ID NO 15
<211> LENGTH: 9
<212> TYPE: PRT
<213> ORGANISM: artificial
<220> FEATURE:
<223> OTHER INFORMATION: Synthetic Construct

<400> SEQUENCE: 15

Arg Glu Leu Leu Leu Thr Cys Ser Gln
1               5

<210> SEQ ID NO 16
<211> LENGTH: 30
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(30)
<223> OTHER INFORMATION: primer

<400> SEQUENCE: 16
gagaaaaatg gtgcctacag catctctcgg                30

<210> SEQ ID NO 17
<211> LENGTH: 29
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(29)
<220> FEATURE:
<221> NAME/KEY: misc_feature
<222> LOCATION: (1)..(29)
<223> OTHER INFORMATION: primer -continued

```
<400> SEQUENCE: 17
agatgctgta ggcaccattt ttctccacg                                              29

<210> SEQ ID NO 18
<211> LENGTH: 23
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(23)
<223> OTHER INFORMATION: primer

<400> SEQUENCE: 18
gacctgcagc tctgggttca tag                                                    23

<210> SEQ ID NO 19
<211> LENGTH: 23
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(23)
<223> OTHER INFORMATION: primer

<400> SEQUENCE: 19
atgaacccag agctgcaggt ctc                                                    23

<210> SEQ ID NO 20
<211> LENGTH: 20
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(20)
<223> OTHER INFORMATION: primer

<400> SEQUENCE: 20
cagagacaca attcaatata                                                        20

<210> SEQ ID NO 21
<211> LENGTH: 17
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(17)
<223> OTHER INFORMATION: primer

<400> SEQUENCE: 21
ttggctcaca tgctttg                                                           17

<210> SEQ ID NO 22
<211> LENGTH: 20
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(20)
<223> OTHER INFORMATION: primer
```

```
<400> SEQUENCE: 22
cgcagatcga tttgaacata                                           20

<210> SEQ ID NO 23
<211> LENGTH: 19
<212> TYPE: DNA
<213> ORGANISM: artificial
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: primer

<400> SEQUENCE: 23
ccgatgtaca atcctcttc                                            19

<210> SEQ ID NO 24
<211> LENGTH: 111
<212> TYPE: PRT
<213> ORGANISM: Homo sapiens
<220> FEATURE:
<221> NAME/KEY: PEPTIDE
<222> LOCATION: (1)..(111)
<223> OTHER INFORMATION: CD44 3MUT

<400> SEQUENCE: 24

Gln Ile Asp Leu Asn Met Thr Cys Arg Phe Ala Gly Val Phe His Val
1               5                   10                  15

Glu Leu Asn Gly Ala Tyr Ser Ile Ser Arg Thr Glu Ala Ala Asp Leu
            20                  25                  30

Cys Lys Ala Phe Asn Ser Thr Leu Pro Thr Met Ala Gln Met Glu Lys
        35                  40                  45

Ala Leu Ser Ile Gly Phe Glu Thr Cys Ser Ser Gly Phe Ile Glu Gly
    50                  55                  60

His Val Val Ile Pro Arg Ile His Pro Asn Ser Ile Cys Ala Ala Asn
65                  70                  75                  80

Asn Thr Gly Val Tyr Ile Leu Thr Ser Asn Thr Ser Gln Tyr Asp Thr
                85                  90                  95

Tyr Cys Phe Asn Ala Ser Pro Pro Glu Glu Asp Cys Thr Ser Val
            100                 105                 110
```